United States Patent
Krag et al.

(10) Patent No.: US 9,399,094 B2
(45) Date of Patent: Jul. 26, 2016

(54) ASSEMBLY COMPRISING SKIN-MOUNTABLE DEVICE AND PACKAGING THEREFORE

(75) Inventors: Christian Røge Krag, Charlottenlund (DK); Jan Harald Preuthun, Brønshøj (DK); Ib Hansen, Herlev (DK); Martin Majdall Petersen, Ølstykke (DK)

(73) Assignee: Novo Nordisk A/S, Bagsvaerd (DK)

( * ) Notice: Subject to any disclaimer, the term of this patent is extended or adjusted under 35 U.S.C. 154(b) by 408 days.

(21) Appl. No.: 12/303,307

(22) PCT Filed: Jun. 1, 2007

(86) PCT No.: PCT/EP2007/055403
§ 371 (c)(1),
(2), (4) Date: Feb. 20, 2009

(87) PCT Pub. No.: WO2007/141210
PCT Pub. Date: Dec. 13, 2007

(65) Prior Publication Data
US 2009/0254041 A1 Oct. 8, 2009

Related U.S. Application Data

(60) Provisional application No. 60/811,197, filed on Jun. 6, 2006.

(30) Foreign Application Priority Data

Jun. 6, 2006 (EP) .................................... 06114979

(51) Int. Cl.
*A61M 5/142* (2006.01)
*A61M 5/158* (2006.01)

(52) U.S. Cl.
CPC ....... *A61M 5/14224* (2013.01); *A61M 5/14248* (2013.01); *A61M 2005/14252* (2013.01); *A61M 2005/1581* (2013.01); *A61M 2005/1587* (2013.01)

(58) Field of Classification Search
CPC ........... A61M 2005/14252; A61M 2005/1581; A61M 2005/1587; A61M 5/14224; A61M 5/14248
USPC .......... 604/180, 174, 171; 206/438, 364, 363, 206/358, 471
See application file for complete search history.

(56) References Cited

U.S. PATENT DOCUMENTS

| 55,711 A | 6/1866 | Regester |
| 69,546 A | 10/1867 | DeFrost |

(Continued)

FOREIGN PATENT DOCUMENTS

| CA | 2239457 | 12/1999 |
| CN | 1612758 | 5/2005 |

(Continued)

OTHER PUBLICATIONS

Search Report issued in connection with counterpart PCT Application No. PCT/ EP2007/053923, mailed Jul. 5, 2007.

(Continued)

*Primary Examiner* — Imani Hayman
(74) *Attorney, Agent, or Firm* — Wesley Nicolas

(57) ABSTRACT

The present invention provides an assembly comprising a skin-mountable device with a mounting surface, the device being arranged in a packaging releasably attached to the device and having an opening through which the device can be moved when detached from the packaging. The device and the packaging comprises cooperating attachment structure, whereby the attachment structure allows the packaging to be moved in parallel with a skin surface for a predetermined distance when a force in parallel with the skin is applied to the packaging in the first direction, yet prevents movement of the packaging away from the general plane. The attachment structure between the packaging and the skin-mountable device, allows the packaging to be used as a handling tool to place the device on a skin surface, the attachment structure preventing that the device inadvertently falls out during handling, yet allows for easy and safe removal.

23 Claims, 12 Drawing Sheets

(56) References Cited

U.S. PATENT DOCUMENTS

| | | |
|---|---|---|
| 123,740 A | 2/1872 | Stevens |
| 858,001 A | 6/1907 | Howe |
| 2,605,765 A | 8/1952 | Kollsman |
| 2,960,097 A | 11/1960 | Scheffler |
| 2,980,032 A | 4/1961 | Schneider |
| 3,705,601 A | 12/1972 | Arisland |
| 4,016,879 A | 4/1977 | Mellor |
| 4,077,405 A | 3/1978 | Haerten et al. |
| 4,137,020 A | 1/1979 | Ito et al. |
| 4,245,634 A | 1/1981 | Albisser et al. |
| 4,262,824 A | 4/1981 | Hrynewycz |
| 4,340,048 A | 7/1982 | Eckenhoff |
| 4,370,305 A | 1/1983 | Affonso |
| 4,378,015 A | 3/1983 | Wardlaw |
| 4,399,824 A | 8/1983 | Davidson |
| 4,402,407 A | 9/1983 | Maly |
| 4,519,792 A | 5/1985 | Dawe |
| 4,529,401 A | 7/1985 | Leslie et al. |
| 4,544,369 A | 10/1985 | Skakoon et al. |
| 4,552,561 A | 11/1985 | Eckenhoff et al. |
| 4,645,491 A | 2/1987 | Evans |
| 4,657,490 A | 4/1987 | Abbott |
| 4,710,170 A | 12/1987 | Haber |
| 4,734,092 A | 3/1988 | Millerd |
| 4,753,651 A | 6/1988 | Eckenhoff |
| 4,755,173 A | 7/1988 | Konopka et al. |
| 4,788,556 A | 11/1988 | Hoisington et al. |
| 4,871,351 A | 10/1989 | Feingold |
| 4,877,034 A | 10/1989 | Atkins et al. |
| 4,886,499 A | 12/1989 | Cirelli et al. |
| 4,894,054 A | 1/1990 | Miskinyar |
| 4,928,528 A | 5/1990 | Marques |
| 4,994,078 A | 2/1991 | Jarvik |
| 5,008,110 A | 4/1991 | Benecke et al. |
| 5,049,146 A | 9/1991 | Bringham et al. |
| 5,076,890 A | 12/1991 | Balembois |
| 5,122,116 A | 6/1992 | Kriesel et al. |
| 5,122,201 A | 6/1992 | Frazier et al. |
| 5,149,340 A | 9/1992 | Waycuilis |
| 5,169,390 A | 12/1992 | Athayde et al. |
| 5,211,201 A | 5/1993 | Kamen et al. |
| 5,224,843 A | 7/1993 | van Lintel |
| 5,256,157 A | 10/1993 | Samiotes et al. |
| 5,336,052 A | 8/1994 | Zöllner et al. |
| 5,390,671 A | 2/1995 | Lord et al. |
| 5,391,950 A | 2/1995 | Krawczak |
| 5,482,473 A | 1/1996 | Lord et al. |
| 5,485,917 A * | 1/1996 | Early .......................... 206/363 |
| 5,494,415 A | 2/1996 | Morita |
| 5,514,095 A | 5/1996 | Brightbill et al. |
| 5,527,288 A | 6/1996 | Gross et al. |
| 5,568,806 A | 10/1996 | Cheney, II et al. |
| 5,584,808 A | 12/1996 | Healy |
| 5,584,813 A | 12/1996 | Livingston et al. |
| 5,586,085 A | 12/1996 | Lichte |
| 5,609,572 A | 3/1997 | Lang |
| 5,647,853 A | 7/1997 | Feldmann et al. |
| 5,720,391 A | 2/1998 | Dohm et al. |
| 5,776,109 A | 7/1998 | Urrutia |
| 5,814,020 A | 9/1998 | Gross |
| 5,851,197 A | 12/1998 | Marano et al. |
| 5,858,001 A | 1/1999 | Tsals et al. |
| 5,860,952 A | 1/1999 | Quinn |
| 5,913,856 A | 6/1999 | Chia et al. |
| 5,925,017 A | 7/1999 | Kriesel et al. |
| 5,928,194 A | 7/1999 | Maget |
| 5,931,814 A | 8/1999 | Alex et al. |
| 5,941,611 A | 8/1999 | Trzmiel et al. |
| 5,954,643 A | 9/1999 | VanAntwerp et al. |
| 5,957,895 A | 9/1999 | Sage et al. |
| 5,968,011 A | 10/1999 | Larsen et al. |
| 5,997,501 A | 12/1999 | Gross et al. |
| 6,045,534 A | 4/2000 | Jacobsen et al. |
| 6,060,319 A | 5/2000 | Deetz et al. |
| 6,074,369 A | 6/2000 | Sage et al. |
| 6,083,196 A | 7/2000 | Trautman et al. |
| 6,088,619 A | 7/2000 | Hein et al. |
| 6,099,512 A | 8/2000 | Urrutia |
| 6,120,492 A | 9/2000 | Finch et al. |
| 6,123,519 A | 9/2000 | Kato et al. |
| 6,126,637 A | 10/2000 | Kriesel et al. |
| 6,132,755 A | 10/2000 | Eicher et al. |
| 6,165,155 A | 12/2000 | Jacobsen et al. |
| 6,241,704 B1 | 6/2001 | Peterson et al. |
| 6,270,478 B1 | 8/2001 | Mernøe |
| 6,280,148 B1 | 8/2001 | Zengerle et al. |
| 6,293,925 B1 | 9/2001 | Safabash et al. |
| 6,302,866 B1 | 10/2001 | Marggi |
| 6,302,869 B1 | 10/2001 | Klitgaard |
| 6,358,731 B1 | 3/2002 | Hsu |
| 6,364,865 B1 | 4/2002 | Lavi et al. |
| 6,485,461 B1 | 11/2002 | Mason et al. |
| 6,500,150 B1 | 12/2002 | Gross et al. |
| 6,551,276 B1 | 4/2003 | Mann et al. |
| 6,554,791 B1 | 4/2003 | Cartledge et al. |
| 6,555,986 B2 | 4/2003 | Moberg |
| 6,558,351 B1 | 5/2003 | Steil et al. |
| 6,589,229 B1 | 7/2003 | Connelly et al. |
| 6,613,015 B2 | 9/2003 | Sandstrom et al. |
| 6,622,037 B2 | 9/2003 | Kasano |
| 6,656,159 B2 | 12/2003 | Flaherty |
| 6,716,192 B1 | 4/2004 | Orosz |
| 6,740,059 B2 | 5/2004 | Flaherty |
| 6,749,587 B2 | 6/2004 | Flaherty |
| 6,808,691 B1 | 10/2004 | Herve et al. |
| 6,818,178 B2 | 11/2004 | Kohl et al. |
| 6,878,136 B2 | 4/2005 | Fleury et al. |
| 6,949,084 B2 | 9/2005 | Marggi et al. |
| 6,960,192 B1 | 11/2005 | Flaherty et al. |
| 7,052,483 B2 | 5/2006 | Wojcik |
| 7,070,580 B2 | 7/2006 | Nielsen |
| 7,097,631 B2 | 8/2006 | Trautman et al. |
| 7,097,690 B2 | 8/2006 | Usher et al. |
| 7,141,023 B2 | 11/2006 | Diermann et al. |
| 7,144,384 B2 | 12/2006 | Gorman et al. |
| 7,303,073 B2 | 12/2007 | Raynal-Olive et al. |
| 7,744,570 B2 | 6/2010 | Fangrow |
| 2001/0025168 A1 | 9/2001 | Gross et al. |
| 2002/0040083 A1 | 4/2002 | Kuwaki et al. |
| 2002/0040208 A1 | 4/2002 | Flaherty et al. |
| 2002/0055711 A1 | 5/2002 | Lavi et al. |
| 2002/0064468 A1 | 5/2002 | Wade |
| 2002/0123740 A1 | 9/2002 | Flaherty et al. |
| 2002/0161332 A1 | 10/2002 | Ramey |
| 2002/0169416 A1 | 11/2002 | Gonnelli et al. |
| 2003/0009131 A1 | 1/2003 | Van Antwerp et al. |
| 2003/0009133 A1 | 1/2003 | Ramey |
| 2003/0029501 A1 | 2/2003 | Williamson et al. |
| 2003/0060781 A1 | 3/2003 | Mogensen et al. |
| 2003/0065308 A1 | 4/2003 | Lebel et al. |
| 2003/0069546 A1 | 4/2003 | Sandstrom et al. |
| 2003/0073952 A1 | 4/2003 | Flaherty et al. |
| 2003/0088238 A1 | 5/2003 | Poulsen et al. |
| 2003/0114797 A1 | 6/2003 | Vaillancourt et al. |
| 2003/0135159 A1 | 7/2003 | Daily et al. |
| 2003/0167035 A1 | 9/2003 | Flaherty et al. |
| 2003/0187395 A1 | 10/2003 | Gabel et al. |
| 2003/0194328 A1 | 10/2003 | Bryant et al. |
| 2003/0199823 A1 | 10/2003 | Bobroff et al. |
| 2003/0216686 A1 | 11/2003 | Lynch et al. |
| 2003/0236498 A1 | 12/2003 | Gross et al. |
| 2004/0051674 A1 | 3/2004 | Mahringer |
| 2004/0087240 A1 | 5/2004 | Chen et al. |
| 2004/0098068 A1 | 5/2004 | Carbunaru et al. |
| 2004/0115068 A1 | 6/2004 | Hansen et al. |
| 2004/0116905 A1 | 6/2004 | Pedersen et al. |
| 2004/0127844 A1 | 7/2004 | Flaherty |
| 2004/0158207 A1 | 8/2004 | Hunn et al. |
| 2004/0162521 A1 | 8/2004 | Bengtsson |
| 2004/0171403 A1 | 9/2004 | Mikkola |
| 2004/0199123 A1 | 10/2004 | Nielsen |
| 2004/0204673 A1 | 10/2004 | Flaherty et al. |
| 2004/0220497 A1 | 11/2004 | Findley et al. |
| 2004/0220536 A1 | 11/2004 | VanTassel et al. |

(56) References Cited

U.S. PATENT DOCUMENTS

| | | | |
|---|---|---|---|
| 2004/0260233 A1 | 12/2004 | Garibotto et al. | |
| 2005/0006309 A1 | 1/2005 | Effenhauser et al. | |
| 2005/0022274 A1 | 1/2005 | Campbell et al. | |
| 2005/0077225 A1 | 4/2005 | Usher et al. | |
| 2005/0101933 A1 | 5/2005 | Marrs et al. | |
| 2005/0171513 A1 | 8/2005 | Mann et al. | |
| 2005/0203461 A1 | 9/2005 | Flaherty et al. | |
| 2005/0240154 A1 | 10/2005 | Mogensen et al. | |
| 2006/0015063 A1* | 1/2006 | Butikofer et al. | 604/93.01 |
| 2006/0017576 A1 | 1/2006 | Gordon et al. | |
| 2006/0020300 A1 | 1/2006 | Nghiem et al. | |
| 2006/0142698 A1 | 6/2006 | Ethelfeld | |
| 2006/0200073 A1 | 9/2006 | Radmer et al. | |
| 2006/0264835 A1 | 11/2006 | Nielsen et al. | |
| 2007/0021733 A1 | 1/2007 | Hansen et al. | |
| 2007/0073228 A1 | 3/2007 | Mernoe et al. | |
| 2007/0104596 A1 | 5/2007 | Preuthun et al. | |
| 2007/0112301 A1 | 5/2007 | Preuthun et al. | |
| 2008/0009805 A1 | 1/2008 | Ethelfeld | |
| 2009/0163874 A1 | 6/2009 | Krag et al. | |
| 2009/0221971 A1* | 9/2009 | Mejlhede | A61M 5/142 604/180 |

FOREIGN PATENT DOCUMENTS

| | | |
|---|---|---|
| DE | 2552446 | 5/1977 |
| DE | 10255817 | 6/2004 |
| DK | PA 2003 00696 | 5/2003 |
| DK | PA 2003 00697 | 5/2003 |
| EP | 20060277 | 3/1986 |
| EP | 398583 | 11/1990 |
| EP | 568176 | 11/1993 |
| EP | 937475 | 8/1999 |
| EP | 1177802 | 2/2002 |
| EP | 1256356 | 11/2002 |
| EP | 1329233 | 7/2003 |
| EP | 1475113 | 11/2004 |
| EP | 1527792 | 5/2005 |
| GB | 2020735 | 11/1979 |
| GB | 2212387 | 7/1989 |
| JP | 2000-104659 | 4/2000 |
| JP | 2000-513259 | 10/2000 |
| JP | 2000-515394 | 11/2000 |
| JP | 2002-505601 | 2/2002 |
| WO | WO 90/07942 | 7/1990 |
| WO | WO 96/07397 | 3/1996 |
| WO | WO 96/30679 | 10/1996 |
| WO | WO 97/21457 | 6/1997 |
| WO | WO 98/57683 | 12/1998 |
| WO | WO 99/62576 | 12/1999 |
| WO | WO 02/02165 | 1/2002 |
| WO | WO 02/04048 | 1/2002 |
| WO | WO 02/05889 | 1/2002 |
| WO | WO02/05889 | 1/2002 |
| WO | WO 02/15889 | 2/2002 |
| WO | WO 02/15965 | 2/2002 |
| WO | WO02/15965 | 2/2002 |
| WO | WO 02/40083 | 5/2002 |
| WO | WO02/45574 | 6/2002 |
| WO | WO02/47746 | 6/2002 |
| WO | WO02/55132 | 7/2002 |
| WO | WO 02/070024 | 9/2002 |
| WO | WO02/081012 | 10/2002 |
| WO | WO02/100457 | 12/2002 |
| WO | WO03000696 | 1/2003 |
| WO | WO03000697 | 1/2003 |
| WO | WO03/026726 | 4/2003 |
| WO | WO03/026728 | 4/2003 |
| WO | WO 03/026728 | 4/2003 |
| WO | WO 03/080169 | 10/2003 |
| WO | WO 03/089028 | 10/2003 |
| WO | WO03/089028 | 10/2003 |
| WO | WO 03/090509 | 11/2003 |
| WO | WO 03/099358 | 12/2003 |
| WO | WO 2004/009160 | 1/2004 |
| WO | WO 2004/029457 | 4/2004 |
| WO | WO2004/029457 | 4/2004 |
| WO | WO 2004/030728 | 4/2004 |
| WO | WO2004/030728 | 4/2004 |
| WO | WO2004/098682 | 11/2004 |
| WO | WO 2004/098683 | 11/2004 |
| WO | WO 2004/101071 | 11/2004 |
| WO | WO 2004098684 A2 * | 11/2004 |
| WO | WO2005/002649 | 1/2005 |
| WO | WO 2005/002649 | 1/2005 |
| WO | WO 2005/011779 | 2/2005 |
| WO | WO 2005/025652 | 3/2005 |
| WO | WO2005/037185 | 4/2005 |
| WO | WO2005/037350 | 4/2005 |
| WO | WO2005/039673 | 5/2005 |
| WO | WO 2005/094919 | 10/2005 |
| WO | WO2005/094919 | 10/2005 |
| WO | WO 2005/123186 | 12/2005 |
| WO | WO 2005/123189 | 12/2005 |
| WO | WO2006/060277 | 6/2006 |
| WO | WO 2006/067217 | 6/2006 |
| WO | WO 2006/077263 | 7/2006 |
| WO | WO 2006/060277 | 8/2006 |
| WO | WO2006/089958 | 8/2006 |
| WO | WO 2006/120253 | 11/2006 |
| WO | WO 2006/123329 | 11/2006 |
| WO | WO2007122207 | 11/2007 |
| WO | WO 2009/021950 | 2/2009 |

OTHER PUBLICATIONS

English language machine translation of JP 2002 505601.
English language machine translation of JP 2000 515394.
Requirement for Restirction in U.S. Appl. No. 11/266,904, Mailed May 22, 2006.
Non-Final Rejection in U.S. Appl. No. 11/266,904, Mailed Jan. 5, 2007.
Final Rejection in U.S. Appl. No. 11/266,904, Mailed Sep. 11, 2007.
First Advisory Action in U.S. Appl. No. 11/266,904, Mailed Dec. 28, 2007.
Second Advisory Action in U.S. Appl. No. 11/266,904, Mailed Aug. 13, 2008.
US 6,197,009, 3/2001, Steg (withdrawn).
International Preliminary Examination Report issued in connection with counterpart PCT Application No. PCT/EP2006/062301, mailed Nov. 22, 2007.
International Search Report and Written Opinion issued in connection with counterpart international application No. PCT/EP2006/062301, mailed Nov. 2, 2006.
International Search Report mailed May 24, 2006 in international application No. PCT/EP2006/050410.
Office Action Issued in Connection With Counterpart Danish Application No. PA 2005 00703, Mailed Mar. 3, 2006.
CN 1612758 English Abstract, published Feb. 6, 2008.
DE 10255817 English Abstract, published Jun. 17, 2004.
JP 2000-104659 Machine Translation, published Apr. 11, 2000.
Final Office Action mailed Apr. 28, 2010 in U.S. Appl. No. 12/066,712, filed Mar. 13, 2008 by Hansen et al.
Non-Final Office Action mailed Oct. 27, 2009 in U.S. Appl. No. 12/066,712, filed Mar. 13, 2008 by Hansen et al.
Non-Final Office Action mailed Apr. 10, 2009 in U.S. Appl. No. 12/066,712, filed Mar. 13, 2008 by Hansen et al.
Final Office Action mailed Jul. 16, 2010 in U.S. Appl. No. 11/913,689, filed Dec. 12, 2007 by Hansen et al.
Non-Final Office Action mailed Mar. 15, 2010 in U.S. Appl. No. 11/913,689, filed Dec. 12, 2007 by Hansen et al.
Final Office Action mailed Nov. 25, 2009 in U.S. Appl. No. 11/913,689, filed Dec. 12, 2007 by Hansen et al.
Non-Final Office Action mailed May 8, 2009 in U.S. Appl. No. 11/913,689, filed Dec. 12, 2007 by Hansen et al.
Non-Final Office Action mailed Apr. 30, 2010 in U.S. Appl. No. 11/911,213, filed Oct. 11, 2007 by Nielsen et al.
Non-Final Office Action mailed Jul. 24, 2009 in U.S. Appl. No. 11/911,213, filed Oct. 11, 2007 by Nielsen et al.

(56) References Cited

OTHER PUBLICATIONS

Final Office Action mailed Nov. 17, 2009 in U.S. Appl. No. 11/816,729, filed Nov. 15, 2007 by Larsen et al.
Non-Final Office Action mailed Apr. 17, 2009 in U.S. Appl. No. 11/816,729, filed Nov. 15, 2007 by Larsen et al.
Non-Final Office Action mailed Jul. 23, 2010 in U.S. Appl. No. 11/813,433, filed Apr. 30, 2008 by Teisen-Simony et al.
Non-Final Office Action mailed Apr. 28, 2010 in U.S. Appl. No. 11/813,381, filed Apr. 11, 2008 by Teisen-Simony et al.
Final Office Action mailed Nov. 3, 2009 in U.S. Appl. No. 11/792,355, filed Apr. 23, 2008 by Ethelfeld et al.
Non-Final Office Action mailed Feb. 17, 2009 in U.S. Appl. No. 11/792,355, filed Apr. 23, 2008 by Ethelfeld et al.
Final Office Action mailed Dec. 29, 2009 in U.S. Appl. No. 11/663,048, filed Nov. 15, 2007 by Thorkild et al.
Non-Final Office Action mailed Apr. 17, 2009 in U.S. Appl. No. 11/663,048, filed Nov. 15, 2007 by Thorkild et al.
Notice of Abandonment mailed Oct. 23, 2007 in U.S. Appl. No. 11/662,905, filed Sep. 22, 2005 by Ahm et al.
Non-Final Office Action mailed May 19, 2010 in U.S. Appl. No. 11/541,348, filed Sep. 29, 2006 by Preuthun et al.
Final Office Action mailed Jan. 8, 2010 in U.S. Appl. No. 11/541,348, filed Sep. 29, 2006 by Preuthun et al.
Non-Final Office Action mailed May 22, 2009 in U.S. Appl. No. 11/541,348, filed Sep. 29, 2006 by Preuthun et al.
Response and Amendment filed Jan. 29, 2009 in U.S. Appl. No. 11/541,348, filed Sep. 29, 2006 by Preuthun et al.
Final Office Action mailed Oct. 29, 2008 in U.S. Appl. No. 11/541,348, filed Sep. 29, 2006 by Preuthun et al.
Response and Amendment filed Jul. 16, 2008 in U.S. Appl. No. 11/541,348, filed Sep. 29, 2006 by Preuthun et al.
Non-Final Office Action mailed Apr. 18, 2008 in U.S. Appl. No. 11/541,348, filed Sep. 29, 2006 by Preuthun et al.
Final Office Action mailed May 5, 2010 in U.S. Appl. No. 11/540,842, filed Sep. 29, 2006 by Preuthun et al.
Non-Final Office Action mailed Sep. 28, 2009 in U.S. Appl. No. 11/540,842, filed Sep. 29, 2006 by Preuthun et al.
Response and Amendment filed Aug. 7, 2009 in U.S. Appl. No. 11/540,842, filed Sep. 29, 2006 by Preuthun et al.
Final Office Action mailed May 13, 2009 in U.S. Appl. No. 11/540,842, filed Sep. 29, 2006 by Preuthun et al.
Response and Amendment filed Mar. 11, 2009 in U.S. Appl. No. 11/540,842, filed Sep. 29, 2006 by Preuthun et al.
Non-Final Office Action mailed Dec. 12, 2008 in U.S. Appl. No. 11/540,842, filed Sep. 29, 2006 by Preuthun et al.
Response and Amendment filed Oct. 10, 2008 in U.S. Appl. No. 11/540,842, filed Sep. 29, 2006 by Preuthun et al.
Final Office Action mailed Jul. 11, 2008 in U.S. Appl. No. 11/540,842, filed Sep. 29, 2006 by Preuthun et al.
Response and Amendment filed May 20, 2008 in U.S. Appl. No. 11/540,842, filed Sep. 29, 2006 by Preuthun et al.
Non-Final Office Action mailed Feb. 25, 2008 in U.S. Appl. No. 11/540,842, filed Sep. 29, 2006 by Preuthun et al.
Final Office Action mailed Aug. 5, 2009 in U.S. Appl. No. 11/407,647, filed Apr. 20, 2006 by Hansen et al.
Non-Final Office Action mailed Feb. 6, 2009 in U.S. Appl. No. 11/407,647, filed Apr. 20, 2006 by Hansen et al.
Final Office Action mailed Sep. 29, 2008 in U.S. Appl. No. 11/407,647, filed Apr. 20, 2006 by Hansen et al.
Non-Final Office Action mailed Feb. 28, 2008 in U.S. Appl. No. 11/407,647, filed Apr. 20, 2006 by Hansen et al.
Non-Final Office Action mailed Aug. 19, 2010 in U.S. Appl. No. 11/266,905, filed Nov. 4, 2005 by Ethelfeld et al.
Final Office Action mailed Oct. 30, 2009 in U.S. Appl. No. 11/266,905, filed Nov. 4, 2005 by Ethelfeld et al.
Non-Final Office Action mailed Mar. 18, 2009 in U.S. Appl. No. 11/266,905, filed Nov. 4, 2005 by Ethelfeld et al.
Non-Final Office Action mailed Aug. 25, 2008 in U.S. Appl. No. 11/266,905, filed Nov. 4, 2005 by Ethelfeld et al.
Final Office Action mailed Oct. 5, 2007 in U.S. Appl. No. 11/266,905, filed Nov. 4, 2005 by Ethelfeld et al.
Non-Final Office Action mailed Mar. 27, 2007 in U.S. Appl. No. 11/266,905, filed Nov. 4, 2005 by Ethelfeld et al.
Notice of Abandonment mailed Oct. 12, 2010 in U.S. Appl. No. 11/266,904, filed Nov. 4, 2005 by Ethelfeld et al.
Notice of Allowance mailed Jul. 15, 2009 in U.S. Appl. No. 11/266,821, filed Nov. 4, 2005 by Ethelfeld et al.
Non-Final Office Action mailed Jan. 29, 2009 in U.S. Appl. No. 11/266,821, filed Nov. 4, 2005 by Ethelfeld et al.
Final Office Action mailed Jul. 18, 2008 in U.S. Appl. No. 11/266,821, filed Nov. 4, 2005 by Ethelfeld et al.
Non-Final Office Action mailed Mar. 28, 2008 in U.S. Appl. No. 11/266,821, filed Nov. 4, 2005 by Ethelfeld et al.
Final Office Action mailed Oct. 16, 2009 in U.S. Appl. No. 11/250,233, filed Oct. 14, 2005 by Ethelfeld et al.
Non-Final Office Action mailed Mar. 12, 2009 in U.S. Appl. No. 11/250,233, filed Oct. 14, 2005 by Ethelfeld et al.
Notice of Abandonment mailed Aug. 31, 2010 in U.S. Appl. No. 10/566,795, filed Aug. 30, 2006 by Radmer et al.
Final Office Action mailed May 4, 2009 in U.S. Appl. No. 10/566,795, filed Aug. 30, 2006 by Radmer et al.
Non-Final Office Action mailed Oct. 17, 2008 in U.S. Appl. No. 10/566,795, filed Aug. 30, 2006 by Radmer et al.
Non-Final Rejection mailed on Apr. 6, 2010 in U.S. Appl. No. 12/298,253, filed Oct. 23, 2008 by Krag et al.

* cited by examiner

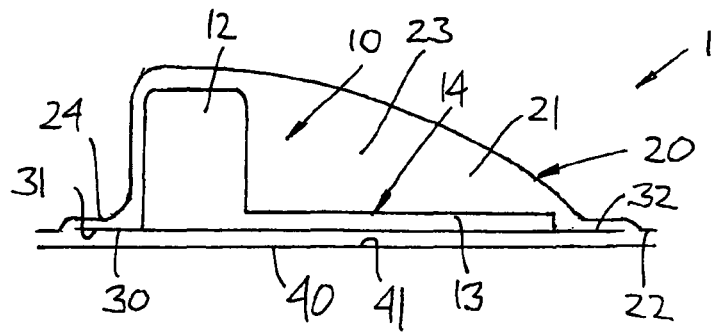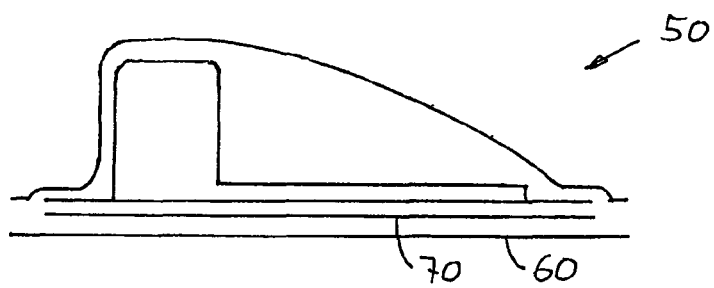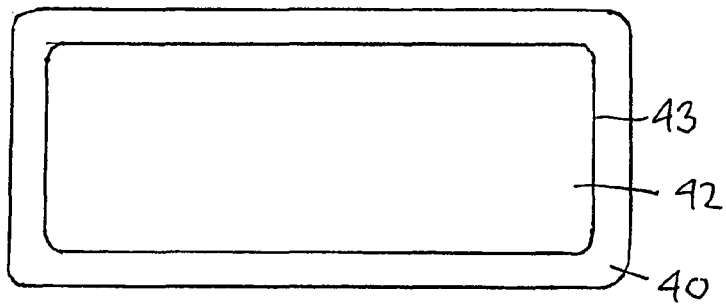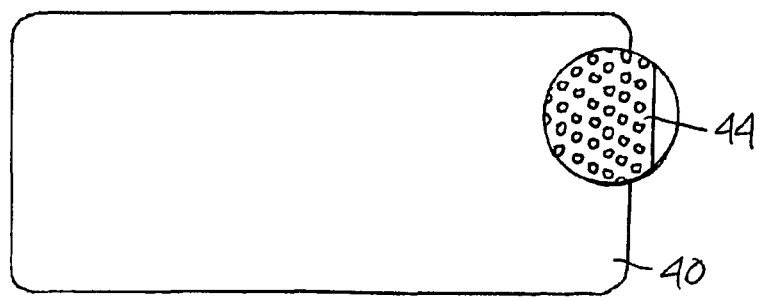

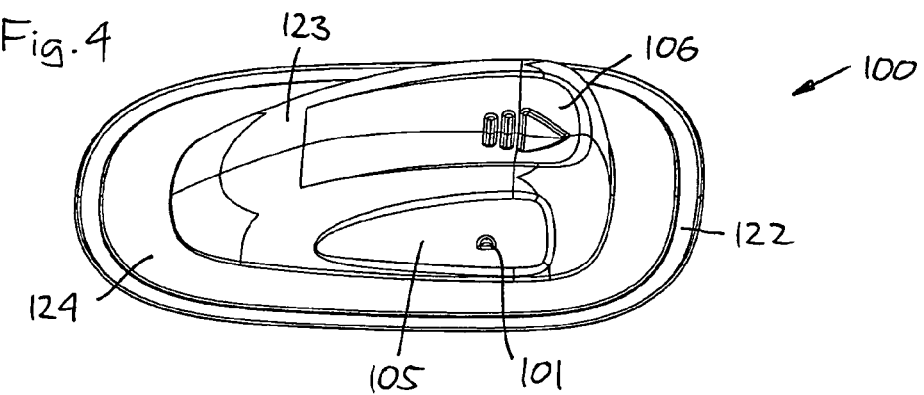
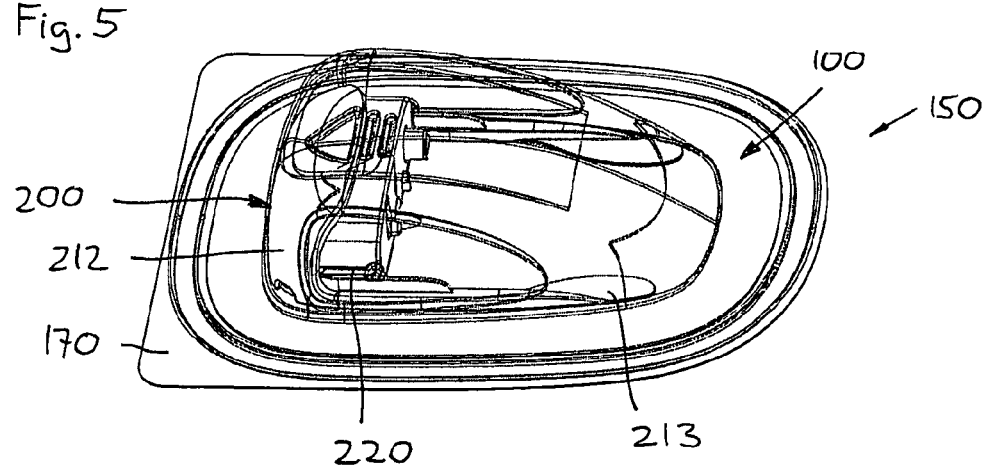

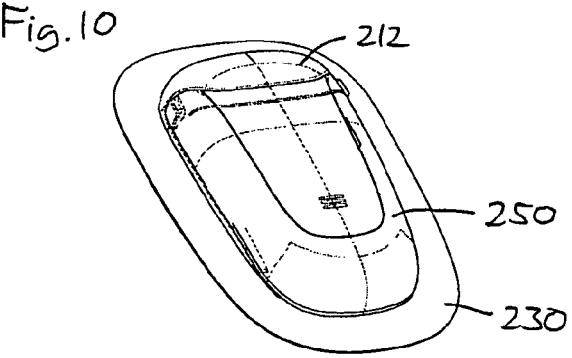
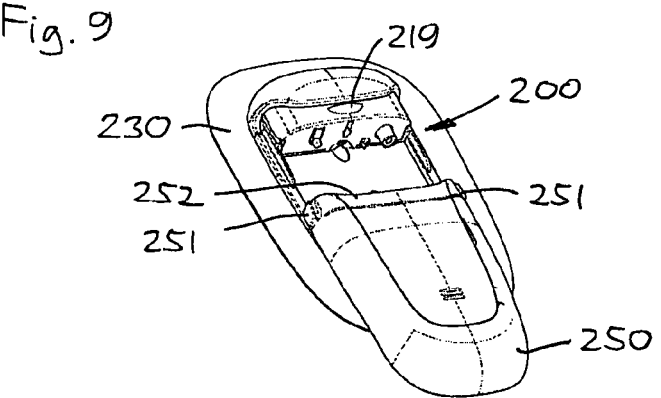

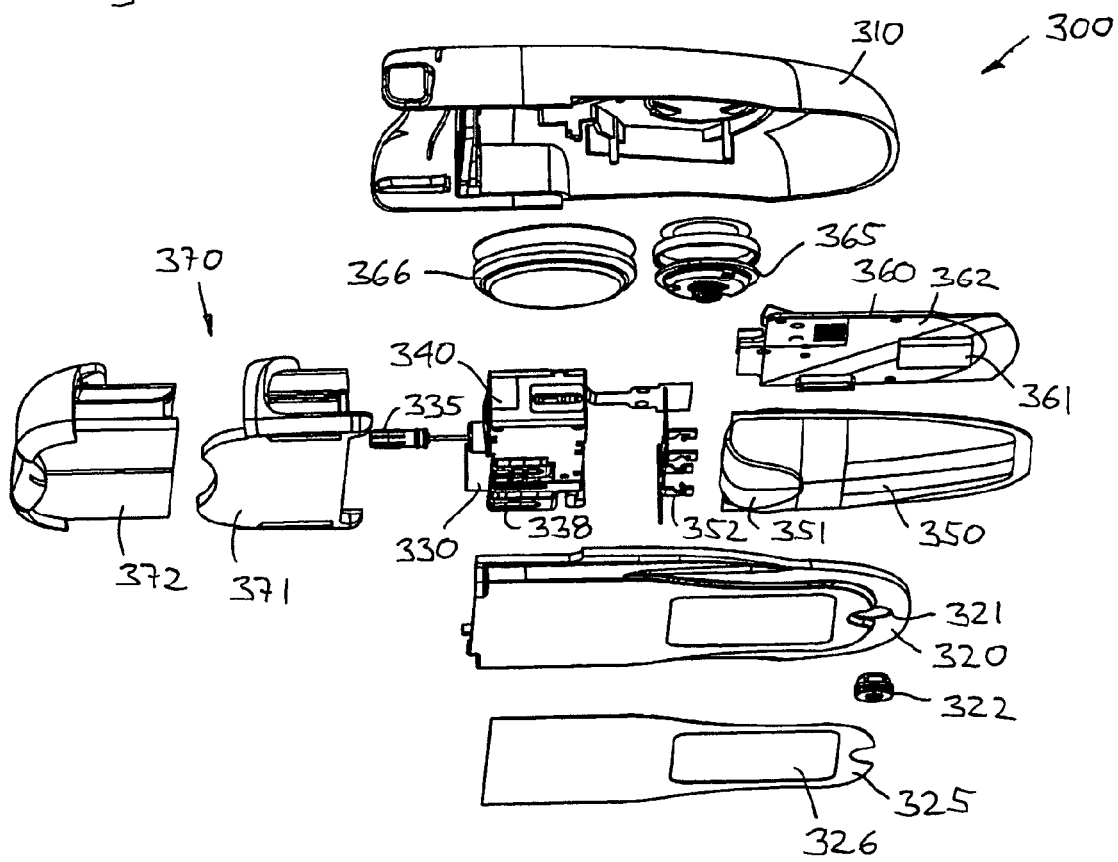

Fig. 14.1
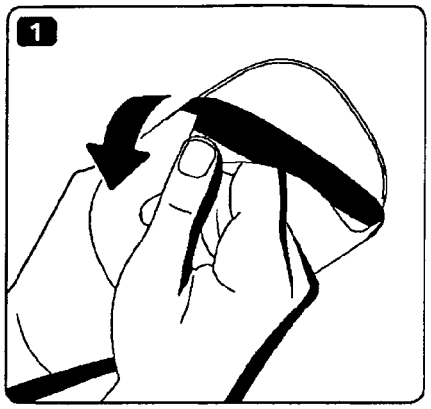
Fig. 14.2
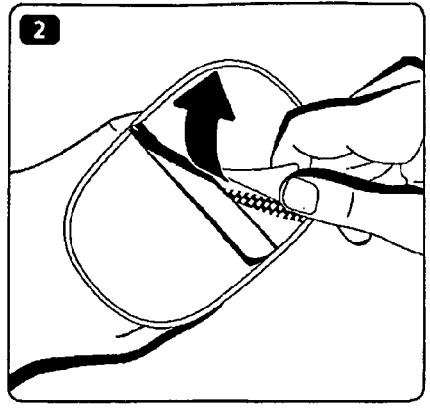
Fig. 14.3
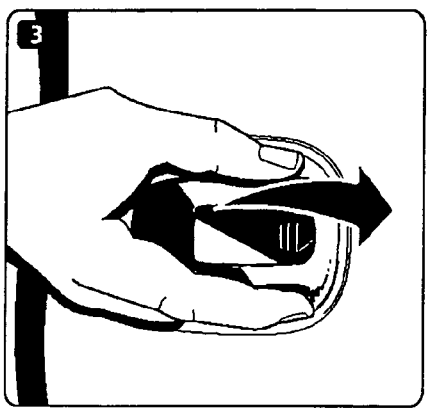
Fig. 14.4
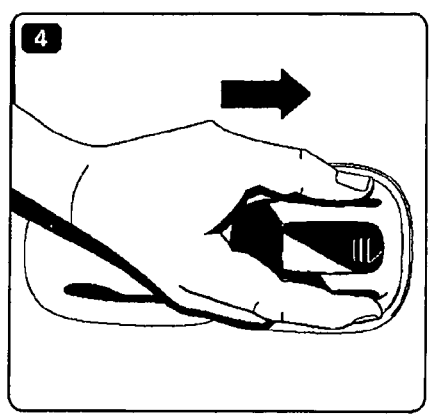
Fig. 14.5
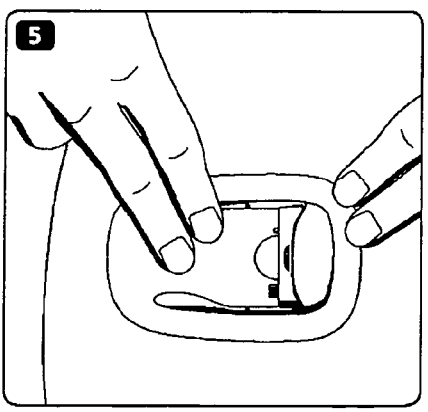
Fig. 14.7
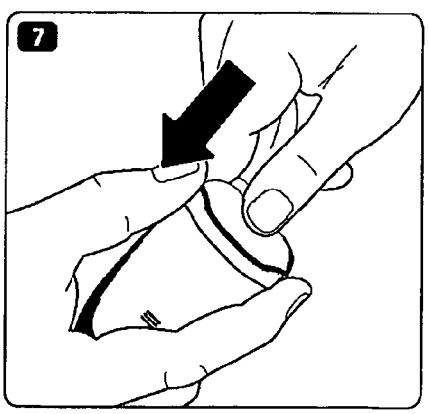

Fig. 14.8
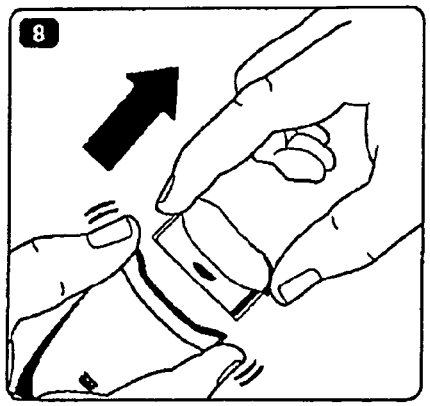
Fig. 14.9
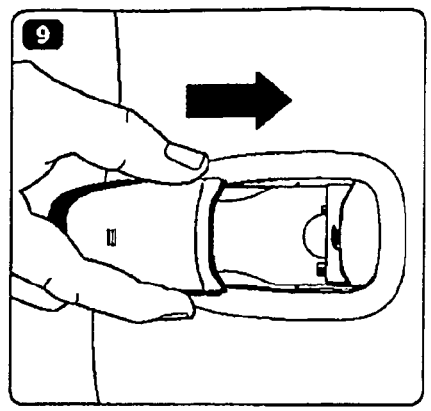
Fig. 18
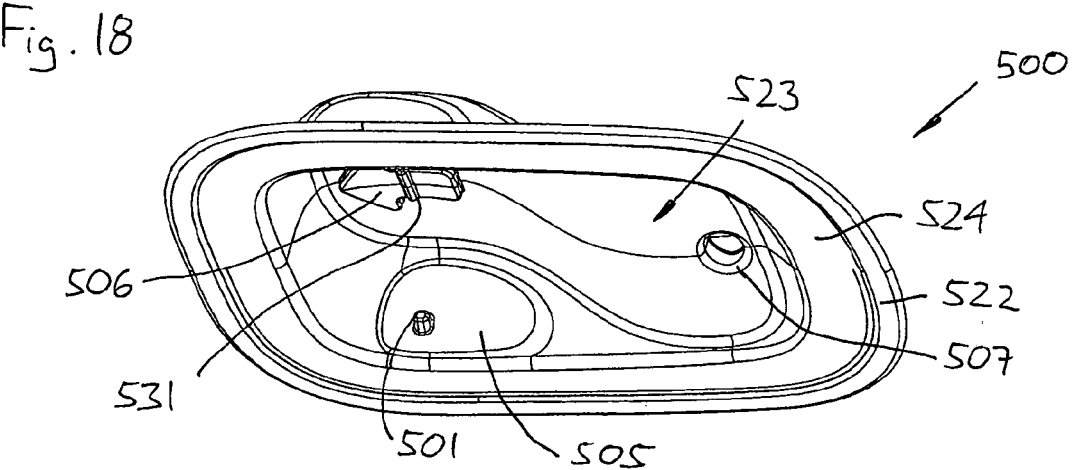
Fig. 19
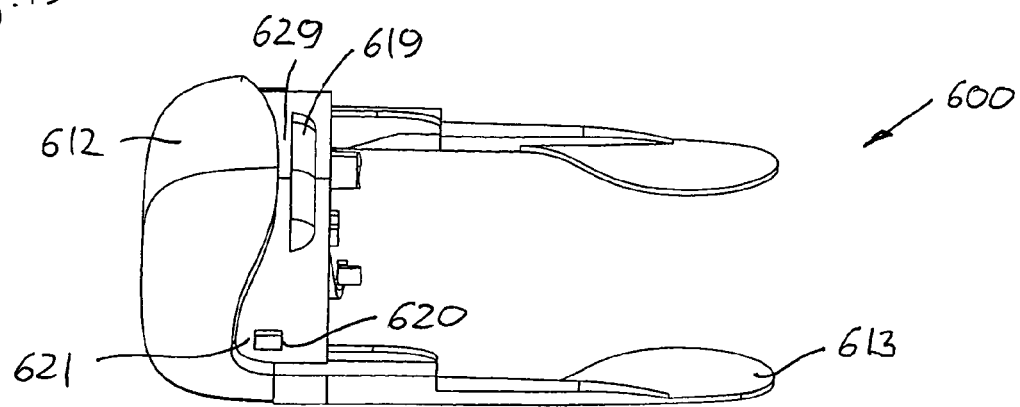

ASSEMBLY COMPRISING SKIN-MOUNTABLE DEVICE AND PACKAGING THEREFORE

CROSS-REFERENCE TO RELATED APPLICATIONS

This application is a 35 U.S.C. §371 national stage application of International Patent Application PCT/EP2007/055403 (published as WO 2007/141210), filed Jun. 1, 2007, which claimed priority of European Patent Application 06114979.5, filed Jun. 6, 2006; this application further claims priority under 35 U.S.C. §119 of U.S. Provisional Application 60/811,197, filed Jun. 6, 2006.

The present invention generally relates to skin-mountable devices. Especially, the invention relates to such devices which are supplied to the user in a packaging, and where the packaging has to be removed prior to taking the device into use.

BACKGROUND OF THE INVENTION

In the disclosure and discussion of the present invention reference is mostly made to the treatment of diabetes by delivery of insulin, however, this is only an exemplary use of the present invention.

Portable drug delivery devices for delivering a drug to a patient are well known and generally comprise a reservoir adapted to contain a liquid drug and having an outlet in fluid communication with a transcutaneous access device such as a soft cannula or a hollow infusion needle, as well as expelling means for expelling a drug out of the reservoir and through the skin of the subject via the cannula or needle, the latter often in the form of an infusion set. Such devices are often termed infusion pumps.

Basically, infusion pumps can be divided into two classes. The first class comprises durable infusion pumps which are relatively expensive pumps intended for 3-4 years use, for which reason the initial cost for such a pump often is a barrier to this type of therapy. Although more complex than traditional syringes and pens, the pump offers the advantages of continuous infusion of insulin, precision in dosing and optionally e.g. programmable delivery profiles and user actuated bolus infusions in connections with meals.

Addressing the above problem, several attempts have been made to provide a second class of drug infusion devices that are low in cost and convenient to use. Some of these devices are intended to be partially or entirely disposable and may provide many of the advantages associated with an infusion pump without the attendant cost and inconveniencies, e.g. the pump may be prefilled thus avoiding the need for filling or refilling a drug reservoir. Examples of this type of infusion devices are known from U.S. Pat. Nos. 4,340,048 and 4,552,561 (based on osmotic pumps), U.S. Pat. No. 5,858,001 (based on a piston pump), U.S. Pat. No. 6,280,148 (based on a membrane pump), U.S. Pat. No. 5,957,895 (based on a flow restrictor pump (also know as a bleeding hole pump), U.S. Pat. No. 5,527,288 (based on a gas generating pump), or U.S. patent (based on a swellable gel) which all in the last decades have been proposed for use in inexpensive, primarily disposable drug infusion devices, the cited documents being incorporated by reference.

The disposable pumps generally comprises a skin-contacting mounting surface adapted for application to the skin of a subject by adhesive means, and with the infusion cannula or needle arranged such that in a situation of use it projects from the mounting surface to thereby penetrate the skin of the user, whereby the place where the needle penetrates the skin is covered while the appliance is in use.

The infusion cannula or needle may be arranged to permanently project from the mounting surface such that the cannula or needle is inserted simultaneously with the application of the infusion pump. Examples of this configuration can be found in U.S. Pat. Nos. 2,605,765 and 4,340,048, and in EP 1 177 802. Although this configuration provides a simple and cost-effective solution, the actual user-performed piercing of the tissue with the needle is often problematic as people who are not experts in medicine are usually insufficiently practised to place such a cannula or needle correctly and they often suffer from a fear of the likely pain.

Addressing the above problem, infusion pump devices have been proposed in which the pump device is supplied to the user with the needle in a retracted state, i.e. with the distal pointed end of the needle "hidden" inside the pump device, this allowing the user to place the pump device on the skin without the possibility of observing the needle. When first the needle is hidden, at least some of the fear is overcome making the introduction of the needle in a second step less problematic. U.S. Pat. Nos. 5,858,001 and 5,814,020 disclose infusion devices of this type in which an infusion needle is arranged in an upper housing portion pivotably arranged relative to a base plate portion. In this way the user can introduce the needle by pressing the upper portion into engagement with the base plate portion.

To further reduce the fear and pain associated with the introduction of the needle, many recent pump devices have been provided with actuatable needle insertion means, which just has to be released by the user after which e.g. spring means quickly will advance the needle through the skin.

For example, U.S. Pat. No. 5,957,895 discloses a liquid drug delivery device comprising a bent injection needle which is adapted to project through a needle aperture in the bottom surface of the housing in a situation of use. A movable needle carrier is disposed in the housing for carrying the injection needle and for causing the injection end of the needle to project through the needle aperture upon movement of the needle carrier.

In the devices disclosed in U.S. Pat. Nos. 5,957,895 and 5,931,814 the needle is automatically inserted by the release of pre-tensioned spring means arranged within the devices, whereas in the device known from WO 02/15965 the needle is inserted by the user actively moving the hidden needle. Further skin-mountable devices which may be used in combination with the present invention are known from e.g. EP 1 527 792, WO 2005/037185, WO 2005/039673, WO 2005/037350, U.S. 6,302,866 and U.S. 2005/0240154, these devices comprising first and second units which in a situation of use is connected to each other forming a single device.

In addition to disclosing different embodiments of a skin-mountable drug delivery device having means for inserting a needle, U.S. Pat. No. 6,960,192 also discloses different embodiments for the fully automatic insertion of a soft cannula, this comprising inserting the cannula with an insertion needle projecting from the distal end, and thereafter retracting the insertion needle.

As the above-described infusion devices all comprise a subcutaneous needle or cannula, the devices have to be supplied to the user in a sterile state, i.e. in a sterile packaging.

Before turning to the disclosure of the present invention, a different type of skin-mountable device will be described.

Although drug infusion pumps, either disposable or durable, may provide convenience of use and improved treatment control, it has long been an object to provide a drug infusion system for the treatment of e.g. diabetes which would rely on closed loop control, i.e. being more or less fully automatic, such a system being based on the measurement of a value indicative of the condition treated, e.g. the blood glucose level in case of insulin treatment of diabetes.

A given monitor system for measuring the concentration of a given substance may be based on invasive or non-invasive measuring principles. An example of the latter would be a non-invasive glucose monitor arranged on the skin surface of a patient and using near-IR spectroscopy.

The sensor may be placed subcutaneously being connected to external equipment by wiring or the substance (fluid) to be analysed may be transported to an external sensor element, both arrangements requiring the placement of a subcutaneous component, the present invention addressing both arrangements. However, for simplicity the term "sensor" is used in the following for both types of sensor elements.

Turning to the sensor elements per se, relatively small and flexible electrochemical sensors have been developed for subcutaneous placement of sensor electrodes in direct contact with patient blood or other extra-cellular fluid (see for example U.S. Pat. No. 5,482,473), wherein such sensors can be used to obtain periodic or continuous readings over a period of time. Insertion devices for this type of sensors are described in, among others, U.S. Pat. Nos. 5,390,671, 5,391,950, 5,568,806 and 5,954,643 which hereby are incorporated by reference.

More specifically, U.S. Pat. No. 5,954,643 discloses an insertion set comprising a mounting base supporting a proximal end of a flexible thin film sensor, the sensor including a distal segment with sensor electrodes thereon which protrudes from the mounting base for transcutaneous placement, wherein the sensor distal segment is slidably carried by a slotted insertion needle fitted through the assembled base. Placement of the insertion set against the patient's skin causes the insertion needle to pierce the skin to carry the sensor electrodes to the desired subcutaneous site, after which the insertion needle can be slidably withdrawn from the insertion set. A similar arrangement is known from U.S. Pat. No. 5,568,806.

DISCLOSURE OF THE INVENTION

Having regard to the above-identified problems, it is an object of the present invention to provide a skin-mountable device which can be supplied to the user in a sealed enclosure, which is convenient to handle and use, and which can be manufactured cost effectively.

In the disclosure of the present invention, embodiments and aspects will be described which will address one or more of the above objects or which will address objects apparent from the below disclosure as well as from the description of exemplary embodiments.

Thus, corresponding to a first aspect, an assembly is provided, comprising a skin-mountable device having a mounting surface for mounting the skin-mountable device to the skin of a subject, the mounting surface defining a general first plane, and a packaging adapted to accommodate the skin-mountable device in an interior thereof and being releasably attached to the skin-mountable device and having an opening through which the skin-mountable device can be moved when detached from the packaging, the opening defining a second plane. The skin-mountable device and the packaging comprise cooperating attachment means, whereby the attachment means allows the packaging to be moved relative to the skin-mountable device in a first direction in parallel with the general plane for a predetermined distance when a force is applied to the packaging in the first direction, yet prevents, corresponding to the attachment means, movement of the packaging away from the general plane. Movement in the first direction may be mainly linear or rotational. If the movement is linear the interior of the packaging may be configured to allow the contained device to slide inside the packaging, or the packaging and device may be configured such that a portion of the device slides out of the packaging as the packaging is moved in the first direction relative to the device.

This arrangement provides a number of advantages. By providing attachment means between the surrounding packaging and the skin-mountable device, the packaging can be used as a handling tool to place the device on a skin surface, the attachment means preventing that the device inadvertently falls out during handling. When the device has been attached to the skin surface, the attachment means provides that the user is "guided" to slide off the packaging instead of merely pulling it off the device in a direction generally perpendicular to the skin surface. By this guided operation it is prevented that the user in an attempt to remove the packaging from the device simply pulls of the device from the skin surface. Further application of a force to the packaging in the first direction may then result in disengagement of the attachment means, this allowing the packaging to be moved away from the device freely without having to overcome the gripping action of the attachment means. In an alternative configuration, further application of a force to the packaging in the first direction results in engagement between an inner inclined surface of the packaging and an upper surface of the skin-mountable device. In this way the packaging can be removed merely by a sliding action.

In an exemplary embodiment the opening in the packaging is arranged substantially corresponding to the general plane, this allowing for simple closure of the opening (see below) as well as securing that the mounting surface is applied to the skin surface together with the packaging.

To improve handling and safety of use the packaging may comprise gripping means associated with the attachment means, whereby application of a force to the gripping means forces the cooperating attachment means into engagement with each other. In this way premature disengagement between the packaging and the device can be prevented during handling.

The cooperating attachment means may comprises a pair of opposed protrusions on either the packaging or the skin-mountable device, and a pair of opposed cooperating grooves arranged on the other of the packaging and the skin-mountable device. In this way a linear guide for movement between the two parts is established.

The assembly may comprise releasable locking means for securing an initial position in which the packaging and the skin-mountable device is attached to each other, the locking means being released when the packaging is moved relative to the skin-mountable device in the first direction.

The packaging may comprise additional release means associated with the attachment means, whereby application of a force to the second gripping means forces the cooperating attachment means from engagement with each other. In this way a second, alternative way of removing the packaging from the device is provided.

The packaging is advantageously in the form of a "blister", i.e. a relatively thin-walled member formed from flexible, normally transparent material by e.g. thermo-forming or injection moulding, this allowing the different portions of the blister packaging engaging the device to flex during operation, e.g. the blister may "snap" into place during assembly or it may "snap" out of engagement with the device during handling by the user.

In exemplary embodiments the mounting surface comprises adhesive means for adhering the skin-mountable device to the skin of the subject, the adhesive means being covered by thereto releasably attached protective means, e.g. a sheet or foil member. The packaging comprises a portion surrounding the opening, and a seal member releasably attached to the surrounding portion, whereby a closed space for the skin-mountable device is provided. The seal member and the protective means may be attached to each other whereby removal of the seal member results in the protective means being removed from the adhesive means. Alternatively, the seal member may have an inner surface releasably attached to the adhesive means, the seal member thereby providing the protective means.

In exemplary embodiments the seal member is penetratable by a sterilizing gas (e.g. ethylene oxide or dry steam), and the inner surface thereof is partially coated with a material allowing the seal member to be peeled from the adhesive means, yet allows the sterilizing gas to penetrate the seal member.

The skin-mountable device may further comprise a transcutaneous device comprising a distal end adapted to be inserted through the skin of a subject, the distal end being moveable between an initial position in which the distal end is retracted relative to the mounting surface, and an extended position in which the distal end projects relative to the mounting surface. The transcutaneous device may be provided in combination with a pointed insertion needle being retractable relative to the transcutaneous device. Such a skin-mountable device may comprise actuation means for moving the distal end of the transcutaneous device between the initial and the extended position when the actuation means is actuated.

In the assembly of the invention the skin-mountable device may be actuatable between an initial state and an actuated state, wherein the skin-mountable device and the packaging comprises cooperating actuation means such that the skin-mountable device is actuated when the packaging is removed from the skin-mountable device. The skin-mountable device may comprise a mechanical mechanism such as a cannula inserter which is actuated when the packaging is removed, or it may comprise electronic components activated when the packaging is removed.

In a further aspect a system is provided comprising two assemblies as described above, wherein the upper portion of the packaging has an outer generally inclined surface, the generally inclined surface being configured so as to allow two assemblies to be arranged on top of each other yin-yang wise.

In a further aspect a system is provided comprising an assembly as described above in combination with a second device, wherein the second device and the skin-mountable device comprises cooperating attachment means. In such a system the skin-mountable device may comprise a transcutaneous device is in the form of a transcutaneous sensor device, and the second device may comprise a processor adapted to transmit and/or process data acquired via the sensor device. Alternatively, the skin-mountable device comprises a transcutaneous device is in the form of a transcutaneous access device, and the second device comprises a reservoir adapted to contain, or containing, a fluid drug, an expelling assembly adapted for cooperation with the reservoir to expel fluid drug out of the reservoir and through the skin of the subject via the transcutaneous access device, and a processor for controlling the expelling assembly. The transcutaneous device may comprise a distal end adapted to be inserted through the skin of a subject, the distal end being moveable between an initial position in which the distal end is retracted relative to the mounting surface, and an extended position in which the distal end projects relative to the mounting surface.

In a yet further aspect an assembly is provided comprising a skin-mountable device with a mounting surface comprising adhesive means for adhering the device to the skin of a subject and defining a general plane, and a packaging releasably attached to the skin-mountable device in an initial position. The packaging comprises an interior space at least partially accommodating the skin-mountable device and having an opening through which the device can be moved when detached from the packaging, and a circumferential portion surrounding the opening and defining a second plane. In such an assembly the second plane is arranged substantially corresponding to the general plane, the device and the packaging comprise co-operating attachment means, and the attachment means allows the packaging to be moved relative to the skin-mountable device in a first direction in parallel with the general plane for a predetermined distance when a force is applied to the packaging in the first direction, yet prevents movement of the packaging away from the general plane.

In a further aspect an assembly is provided comprising a skin-mountable device having a mounting surface for mounting the skin-mountable device to the skin of a subject, the mounting surface defining a first general plane, and a blister packaging adapted to accommodate the skin-mountable device in an interior thereof and being releasably attached to the skin-mountable device. The blister packaging comprises a lower opening through which the skin-mountable device can be moved when detached from the packaging, the opening defining a second plane. In such an assembly the skin-mountable device and the packaging comprises cooperating attachment means, the attachment means allowing the packaging to be rotated relative to the skin-mountable device in a first direction generally perpendicular relative to the general plane for a predetermined angle, and further rotation of the packaging in the first direction results in disengagement of the attachment means, this allowing the packaging to be moved away from the general plane.

In a further aspect of the invention a packaging as described above is provided per se.

In a yet further aspect a method for mounting a skin-mountable device to the skin of a subject is provided, comprising the steps of (a) providing an assembly comprising (i) a skin-mountable device having an adhesive mounting surface defining a general plane, (ii) a blister packaging releasably attached to the skin-mountable device and comprising an opening through which the skin-mountable device can be moved when detached from the packaging, and (iii) cooperating attachment means arranged between the skin-mountable device and the packaging, the attachment means allowing the packaging to be moved relative to the skin-mountable device in a first direction in parallel with the general plane for a predetermined distance when a force is applied to the packaging in the first direction. The method comprising the further steps of (b) applying the assembly towards the skin thereby attaching the mounting surface to the skin, (c) applying a force to the packaging in the first direction such that the packaging is moved in the first direction in parallel with the general plane for the predetermined distance, and (d) applying further force to the packaging in the first direction, this resulting in disengagement of the attachment means, whereby the packaging can be moved away from the general plane.

In a second aspect an assembly is provided comprising (a) a skin-mountable device having a mounting surface comprising adhesive means for adhering the device to the skin of a subject, and (b) a packaging comprising an opening through which the skin-mountable device can be moved when removed from the packaging, the opening defining a general plane, the mounting surface being arranged substantially corresponding to the general plane, and a circumferential portion surrounding the opening. The assembly further comprises (c) a seal member releasably attached to the surrounding portion, thereby providing a closed space for the skin-mountable device, the seal member having an inner surface being releasably attached to the adhesive means, the seal member being penetratable by a sterilizing gas, wherein the inner surface is partially coated with a material allowing the seal member to be peeled from the adhesive means, yet allows the sterilizing gas to penetrate the seal member. In this way a seal member is provided which to a high degree has both of the desired properties, i.e. being gas penetratable yet allows the seal member to be peeled from the adhesive surface. Corresponding to the coated areas, the coating may limit or fully block gas penetration. The packaging may be releasably attached to the skin-mountable device by attachment means.

The mounting surface may have an area which is smaller than the area of the lower opening of the packaging, whereby a gas penetration area is defined between at least a portion of the circumference of the mounting surface and the circumferential portion of the packaging. In an exemplary embodiment the coating is arranged substantially corresponding to the area of the inner surface of the seal member attached to the mounting surface. The coating may be applied in a fine pattern, the pattern providing a surface allowing the sterilizing gas to penetrate the seal member, yet allows the seal member to be removed from the mounting surface.

The skin-mountable device may comprise a housing portion mounted to a flexible sheet member provided with an adhesive layer on its lower surface, the sheet member extending laterally relative to at least a portion of the circumference of the housing portion. The sheet member may have a form and size substantially corresponding to the form and size of the lower opening of the packaging. In such a configuration, at least a portion of the sheet member extending laterally from the housing portion may be permeable to the sterilizing gas.

In exemplary embodiments an assembly as described above, the skin-mountable device further comprising a transcutaneous device comprising a distal end adapted to be inserted through the skin of a subject, the distal end being moveable between an initial position in which the distal end is retracted relative to the mounting surface, and an extended position in which the distal end projects relative to the mounting surface. The transcutaneous device may be provided in combination with a pointed insertion needle being retractable relative to the transcutaneous device, and the skin-mountable device may comprises actuation means for moving the distal end of the transcutaneous device between the initial and the extended position when the actuation means is actuated.

As used herein, the term "drug" is meant to encompass any drug-containing flowable medicine capable of being passed through a delivery means such as a hollow needle in a controlled manner, such as a liquid, solution, gel or fine suspension. Representative drugs include pharmaceuticals such as peptides, proteins, and hormones, biologically derived or active agents, hormonal and gene based agents, nutritional formulas and other substances in both solid (dispensed) or liquid form. In the description of the exemplary embodiments reference will be made to the use of insulin. Correspondingly, the term "subcutaneous" infusion is meant to encompass any method of transcutaneous delivery to a subject. Further, the term needle (when not otherwise specified) defines a piercing member adapted to penetrate the skin of a subject.

BRIEF DESCRIPTION OF THE DRAWINGS

In the following the invention will be further described with references to the drawings, wherein FIG. 1 shows a first assembly comprising a skin-mountable device arranged in a packaging, FIGS. 2A and 2B show embodiments of a seal member having an inner partially coated surface, FIG. 3 shows a second assembly comprising a skin-mountable device arranged in a packaging, FIG. 4 shows a further embodiment of a packaging, FIG. 5 shows in an X-ray representation an assembly comprising a packaging of the same type as in FIG. 4 in which a patch unit is arranged, FIG. 9 shows a patch unit with a pump unit partly attached, FIG. 10 shows the pump unit of FIG. 9 fully attached to the patch unit, FIG. 13 shows in an exploded view a pump unit, FIGS. 14.1-14.5 and 14.7-14.9 show the application of a skin-mountable patch device utilizing aspects of the present invention, FIG. 18 shows a yet further embodiment of a packaging, and FIG. 19 shows a further embodiment of a patch unit.

In the figures like structures are identified by like reference numerals.

DESCRIPTION OF EXEMPLARY EMBODIMENTS

Figure 6:
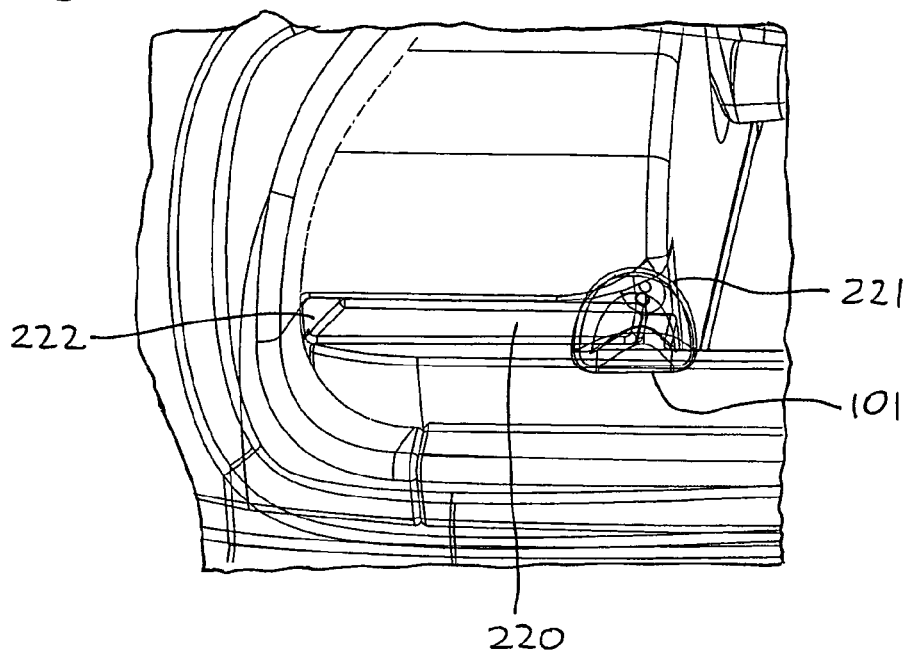
FIG. 6 shows a partial enlargement of a detail of FIG. 5.

When in the following terms as "upper" and "lower", "right" and "left", "horizontal" and "vertical" or similar relative expressions are used, these only refer to the appended figures and not necessarily to an actual situation of use.

FIG. 1 discloses an assembly 1 comprising a skin-mountable device 10 arranged in a packaging 20. The device comprises a relatively rigid body portion 14. arranged on a flexible sheet member 30 with a lower mounting surface 31 provided with a medical grade adhesive material or composition allowing the sheet to be adhered to a skin surface of a subject. The body portion comprises a housing portion 12 having two slider leg members 13 extending there from (see FIG. 7). The sheet member, which may be mono- or multilayered and may comprise both woven and non-woven materials, has a larger footprint than the body portion thereby providing a flexible peripheral portion 32 extending from the body portion. The body portion may be attached to the sheet member by any suitable means, e.g. welding or adhesive.

In the shown embodiment the packaging is in the form of a thermoformed blister packaging forming a cavity 21 to accommodate the device, however, the blister may be injection moulded or formed by any other suitable process. The packaging comprises a lower opening through which the skin-mountable device can be moved when removed from the packaging, the opening defining a general plane, and a circumferential portion 22 surrounding the opening. In the shown embodiment the cavity corresponds to the specific configuration of the enclosed device, i.e. comprising an asymmetrical relatively deep central cavity portion 23 for accommodating the body portion, and an outer relative flat peripheral portion 24 for accommodating the peripheral portion of the sheet member, whereby the mounting surface is arranged substantially corresponding to the general plane. The asymmetrical cavity portion comprises a deep portion for accommodating the housing, and a less deep portion for accommodating the leg members, the upper surface having an inclined configuration relative to the length orientation of the packaging.

A seal member 40 is releasably attached to the circumferential portion 22 of the packaging, thereby providing a closed space for the skin-mountable device. The seal member may be attached to the packaging by any suitable means, e.g. welding or adhesive. In the shown embodiment the seal member has an inner surface 41 releasably attached to the adhesive means, whereby the seal member also serves as a protective peel liner for the adhesive mounting surface. The seal member is penetratable by a sterilizing gas (e.g. ethylene oxide or dry steam), and has an inner surface partially coated with a material allowing the seal member to be easily peeled from the adhesive means (e.g. silicone), yet allows the sterilizing gas to penetrate the seal member corresponding to the non-coated portions and enter the interior of the packaging. In this way a seal member is provided which to a high degree has both of the desired properties, i.e. being gas penetratable yet allows the seal member to be peeled from the adhesive surface. Corresponding to the coated areas, the coating may limit or fully block gas penetration. In an exemplary embodiment the sealing member is made from Tyvek ® which has very good properties as a gas penetratable sealing material, yet would normally stick to an adhesive surface. However, by applying a coating as set out above, e.g. silicone applied using a printing process, the Tyvek ® surface can be provided with slip properties allowing it to be peeled from the adhesive mounting surface.

The coating may be applied in different configurations. In a first embodiment the coating is applied corresponding to the attachment zone 42 for the sheet member, this leaving a non-coated area 43 corresponding to the gap between the sheet member and the circumferential portion of the packaging (see FIG. 2A). In an alternative embodiment the coating is applied in a fine pattern (e.g. a dot pattern 44), the pattern providing a surface allowing the sterilizing gas to penetrate the seal member, yet allows the seal member to be removed from the mounting surface (see FIG. 2B). Such a pattern may be applied corresponding to the attachment zone for the sheet member, or it may be applied to the entire inner surface of the seal member, this allowing a uniformly coated material to be used for the seal member. Indeed, in the latter case the coating should not interfere with the ability of the seal member material to be sealed to the packaging. If the coated area corresponding to the sheet member is not fully blocking for gas penetration and also the sheet member and the adhesive on the mounting surface allows gas penetration to a certain degree, then the sterilizing process would not have to rely only on gas entrance through the gap between the sheet member and the packaging.

Figure 2C:
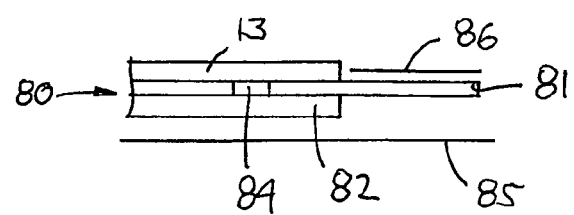
FIG. 2C shows a flexible sheet member of a two layered construction.

FIG. 2C discloses an embodiment in which a flexible sheet member 80 is of a two layered construction comprising an upper, thin flexible film 81 (e.g. a permeable polyurethane film with a lower adhesive surface) arranged on a main carrier 82 (e.g. a permeable flexible polyurethane material with a lower adhesive surface. To properly weld the parts together, the film may comprise one or more openings 84 allowing the body 13 to be welded directly to the carrier corresponding to the opening(s). In addition to the lower release liner 85 an upper circumferential release liner 86 is provided to support the thin film during mounting to the skin surface.

In FIG. 3 an embodiment 50 is shown in which separate seal member 60 and peel liner 70 are used. The liner and the seal member may be arranged such that peeling off the seal member automatically result in the liner being peeled of, this irrespective of the position of the mounting surface.

FIG. 4 shows an embodiment of a packaging 100 provided with a set of opposed attachment means 101 allowing a skin-mountable device comprising cooperating attachment means to be mounted in the interior cavity of the packaging and releasably attached thereto. The packaging is of the same general configuration as the packaging shown en FIG. 1, comprising an asymmetrical relatively deep central portion 123, an outer relative flat peripheral portion 124, and a circumferential portion 122. As the packaging may comprise a sharp outer edge, the outer-most portion of the circumferential portion is bent slightly upwards to avoid irritating the skin when placed thereon. On each side of the packaging a shallow depression 105 is provided on which attachment means en the form of a rounded inwards protrusion 101 is arranged, the two depression providing first gripping means. By attaching the packaging to the enclosed skin-mountable device, the packaging can be used as an applicator for mounting the contained device to a skin surface. The packaging further comprises a number of depressions on the upper surface forming an indicia 106 in the form of an arrow. This area of the packaging may also serve as a release means such that depression thereof results in the side surfaces with the protrusions being lifted away from the grooves, thereby releasing the attachment between the device and the packaging.

FIG. 5 shows in an X-ray representation an assembly 150 comprising a packaging 100 of the same type as in FIG. 4, in which a skin mountable device in the form of a patch unit 200 is arranged, the packaging cavity being closed by a seal member 170. The seal member may be a combined seal member as in FIG. 1 or a separate seal member as in FIG. 3. The patch unit 200 has the same general configuration as shown in FIG. 1, however, it is provided with additional attachment means in the form of a set of opposed grooves 220 adapted to cooperate with the packaging protrusions 101. As seen in FIG. 6 the groove has a first end 221 in which the protrusion 101 is arranged in an initial position when supplied to the user, and a second end 222. When the packaging is pushed in the direction of the housing portion, the protrusions will slide in the groove until they engage the second end at which point they are forced outwardly and thereby disengage the groove and the packaging will become detached from the device. As appears from e.g. FIG. 5, the portion 212 of the housing portion facing away from the leg members 213 is arranged in closed proximity to the packaging, this preventing the packaging from sliding in the opposite direction. Indeed, in an alternative configuration, the attachment means may be configured to be released by movement of the packaging in more than one direction, e.g. back or forth.

When movement between the packaging and the device is linear the interior of the packaging may be configured to allow the contained device to slide inside the packaging, or the packaging and device may be configured such that a portion of the device slides out of the packaging as the packaging is moved in the first direction relative to the device. In the shown embodiment the leg members 213 may slide out of the interior of the package as the package slides in the grooves before it is released from the device.

Figure 7:
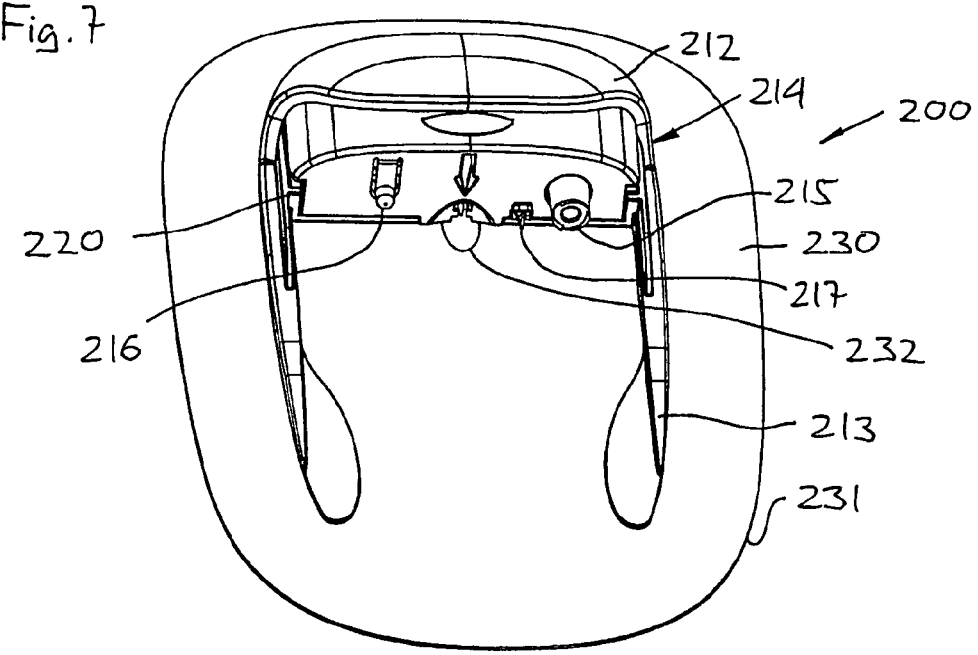
FIG. 7 shows the patch unit of FIG. 5 in greater detail.
Figure 8:
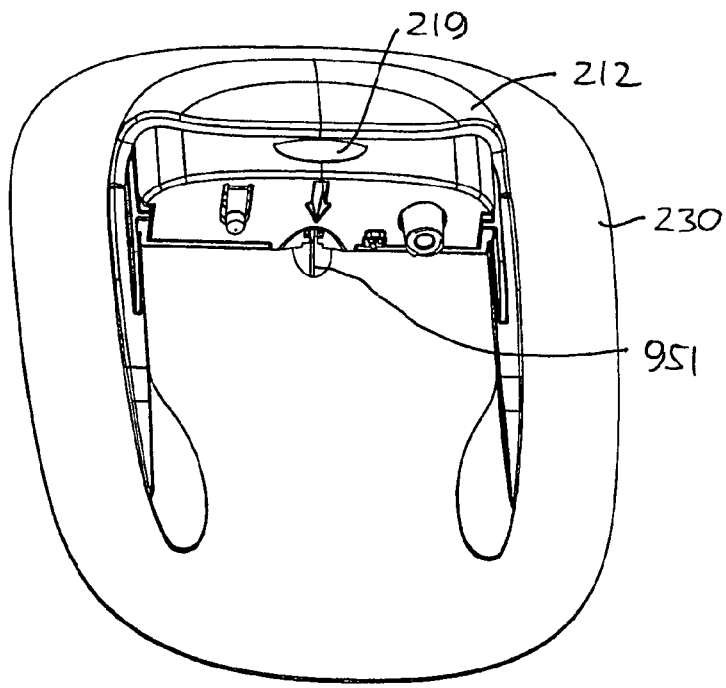
FIG. 8 shows the patch unit of FIG. 7 in an actuated state.

FIG. 7 shows the patch unit 200 in greater detail. The patch unit comprises a relatively rigid body portion 214 arranged on a flexible sheet member 230 with a lower mounting surface 231 provided with an adhesive allowing the sheet to be adhered to a skin surface of a subject. The sheet member comprises a central opening 232 through which a cannula can be inserted. The body portion comprises a housing portion 212 in which a cannula inserting mechanism is arranged, see below. The body portion further comprises two slider leg members 213 extending from the housing, the legs adding stiffness to the patch and further serves as guiding means when a pump/reservoir unit is attached to patch unit, see below. The housing is provided with a set of opposed grooves 220 serving as attachment means for a packaging and subsequently for a pump unit. The housing further comprises a fluid inlet 215 adapted to be mounted in fluid communication with a corresponding fluid outlet from an attached pump unit 250 (see FIG. 9), an actuator 216 for actuating an electrical contact on the attached pump, and a release member 217 adapted to release a cannula inserting mechanism when the pump unit is attached for the first time, the cannula being inserted through the opening 232. The housing portion 212 also comprises a catch 219 adapted to engage a corresponding coupling structure 252 on the pump unit. As appears, when the cannula 951 is inserted, it is protected by the pump unit, however, the pump unit can be removed for subsequent inspection of the insertion site as shown in FIG. 8.

FIG. 9 shows the patch unit 200 with the pump unit 250 partly attached, and FIG. 10 shows the pump unit fully but releasably attached. In order to release the pump unit from the patch unit, the user depresses a set of knobs 251 on the pump unit, this slightly lifting the coupling "bridge" 252 away from the catch 219 on the patch unit housing.

Figure 11:
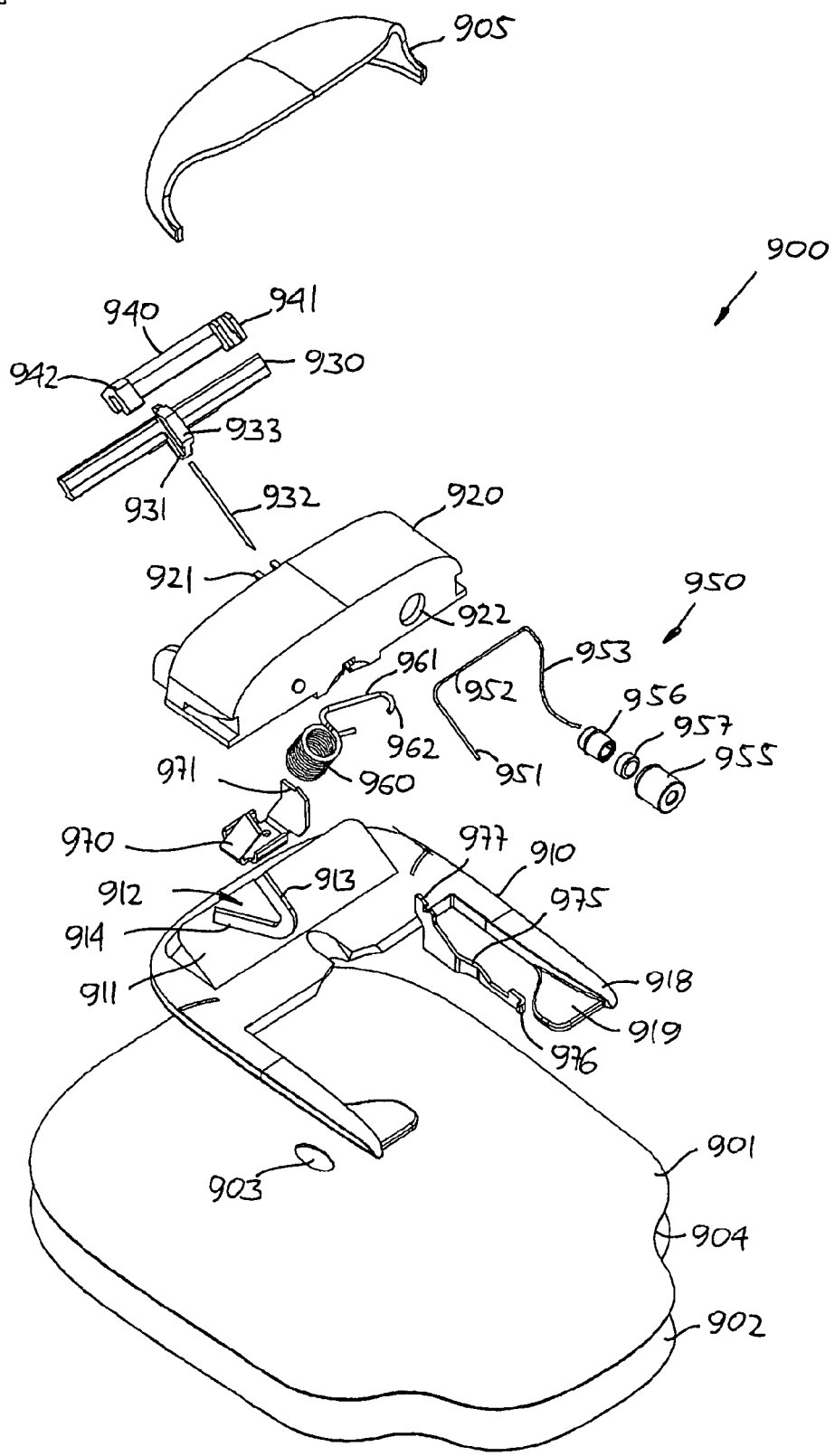
FIG. 11 shows in an exploded view a schematic representation of a transcutaneous device unit.

FIG. 11 shows in an upper exploded view a drawing of a schematic representation of a transcutaneous device unit (here a cannula unit) comprising a mechanism for inserting a soft cannula. More specifically, the unit comprises a bottom part 910 onto which is mounted a chassis part 920 thereby creating an interior in which the different parts of the mechanism are arranged. In addition to the functional portions of the bottom and chassis part the mechanism comprises a needle holder 930 with a needle mount 931 to which a needle 932 is mounted, a cannula holder 940 comprising first and second gripping portions 941, 942 adapted to engage the needle holder, and a hollow cannula assembly comprising a soft, flexible cannula with a distal portion 951, an intermediate portion 952, and a proximal portion 953, the cannula assembly further comprising a tubular housing member 955 adapted to engage an opening 922 in the chassis portion, an elastomeric tubular member 956 in which the proximal end of the cannula is mounted, and a needle pierceable elastomeric septum, the tubular member and the septum being arranged in the housing member thereby providing a fluid inlet port for the hollow cannula. The mechanism further comprises a coil-formed torsion spring 960 comprising an actuator arm 961 with a curved distal end 962, the spring being arranged in a spring holder 970 comprising a catch 971 allowing the spring to be mounted in a pre-tensioned state. A release member 975 is provided comprising an outer end portion 976 adapted to engage e.g. a pump unit when the latter is mounted, and an inner end portion 977 adapted to engage and release the actuator arm from the spring holder. The bottom part comprises an inclined surface 914. with a guide 912 comprising a first guide groove 913 arranged corresponding to a longitudinal axis of the unit, and a second guide groove 914 arranged at an angle of 45 degrees relative to the first guide groove.

In the assembled state the cannula holder is mounted on the needle holder with the gripping portions 941, 942 arranged on each side of the needle mount 931, this allowing the cannula holder to slide along the length of the needle holder, the two holders thereby forming an inserter. In an initial state the distal portion of the cannula is positioned in the needle and the intermediate portion is positioned in a channel formed between the needle holder and the cannula holder, the cannula being mounted to the cannula holder by means of a flexible member on the first gripping portion.

In the assembled state the needle holder with the cannula holder mounted is arranged on the inclined surface and is allowed to slide up and down, with the guide grooves adapted to engage a guide member arranged on the lower surface of the cannula holder (not shown, see e.g. FIG. 24). To control movement of the needle holder the needle mount comprises a guide portion 933 with two opposed grooves adapted to engage a corresponding guide member 921 arranged on an interior surface of the chassis part. As appears, in the shown schematic drawing the inclined surface 914 is shown without cut-out portions allowing the release member 975 and the spring holder 970 to be mounted (see below).

The bottom part 910 further comprises two opposed leg portions 918 each with a lobe 919, the lobes providing attachment points when the bottom part is mounted to a flexible sheet or foil member 901 comprising an adhesive lower mounting surface 904 allowing the transcutaneous unit to be mounted on a skin surface of a subject. The sheet member comprises a central opening 903 through which the needle and cannula is introduced, as well as a release liner 902. A cover portion 905 serves to close the interior thereby forming a substantially closed housing.

With reference to FIGS. 12A-12D the mechanism described with reference to FIG. 11 is shown in a partly assembled state, the chassis part and the proximal portion of the cannula not being shown. The assembled embodiment differs slightly from the above-described embodiment, however, as the differences are small the same reference numerals are used.

The assembled embodiment primarily differs from the FIG. 11 embodiment in that the inclined surface 914. has been replaced with a number of wall members, the upper surfaces of these wall members in combination providing an inclined "surface" on which the needle holder is arranged, this allowing the spring 960 and release member 975 to be shown functionally correctly arranged.

Figure 12A:
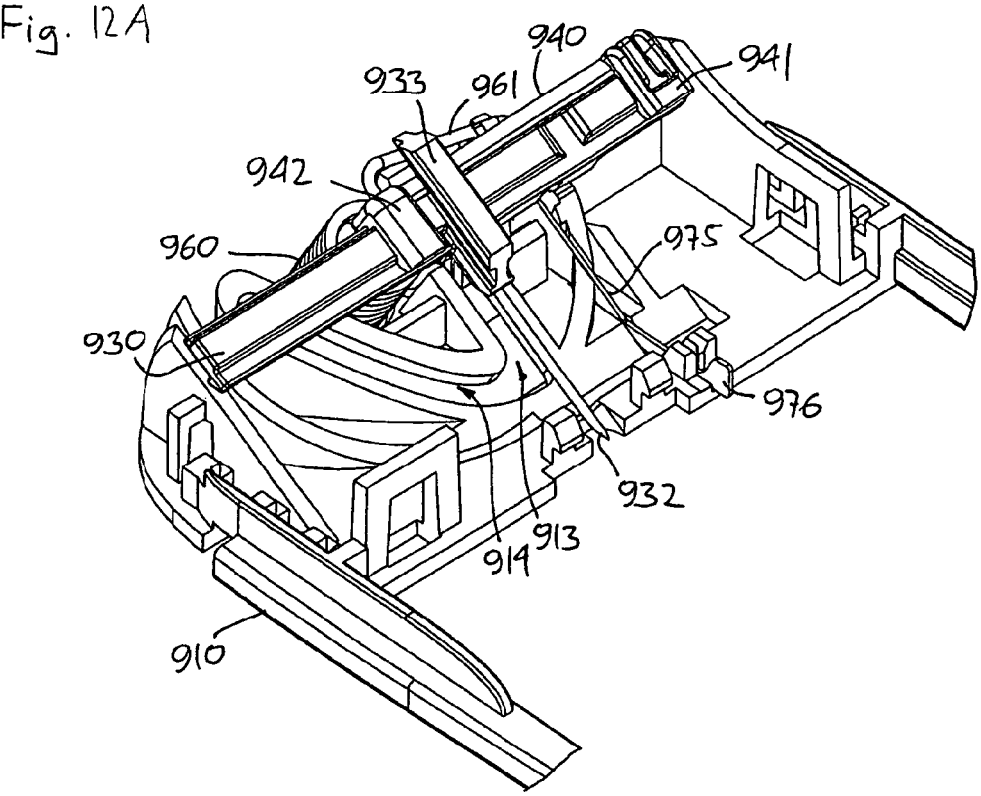
FIGS. 12A-12D show in different actuation states a mechanism for insertion of a cannula.

FIG. 12A shows the assembly in an initial state with the needle holder 930 in a first (or initial) retracted position with the needle correspondingly in its retracted position with the distal pointed end arranged within the housing. The cannula holder is positioned in a right-most position on the needle holder corresponding to its retracted position. The distal portion of the cannula is positioned in the needle with the distal end just within the distal end of the needle, and the intermediate portion is positioned in the channel formed between the needle holder and the cannula holder (see FIG. 24), the cannula being gripped by a flexible arm formed as part of the first gripping member 941.

Figure 12B:
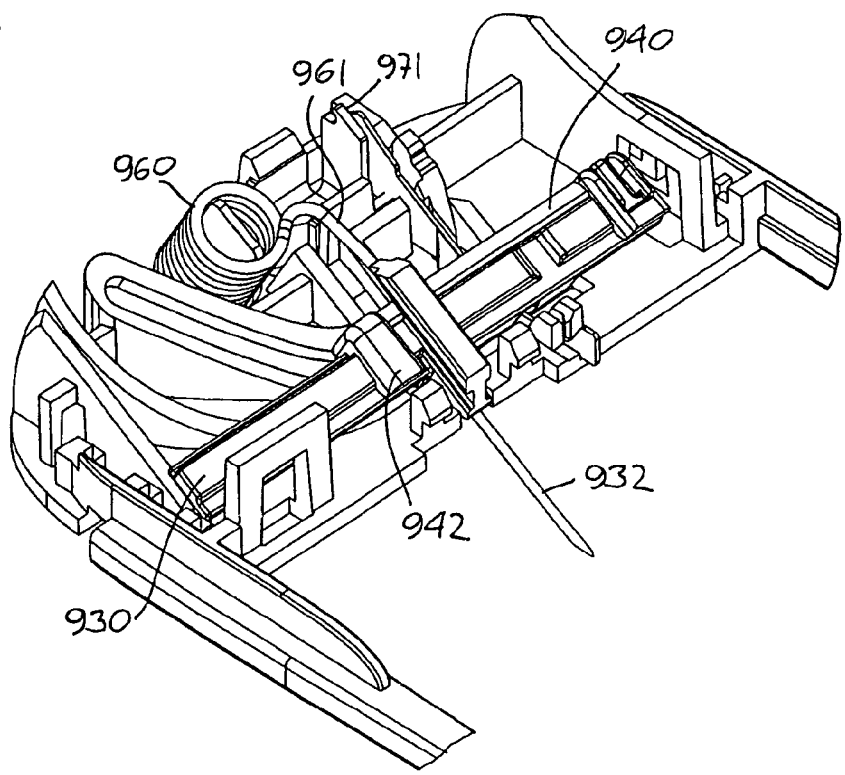
Figure 12C:
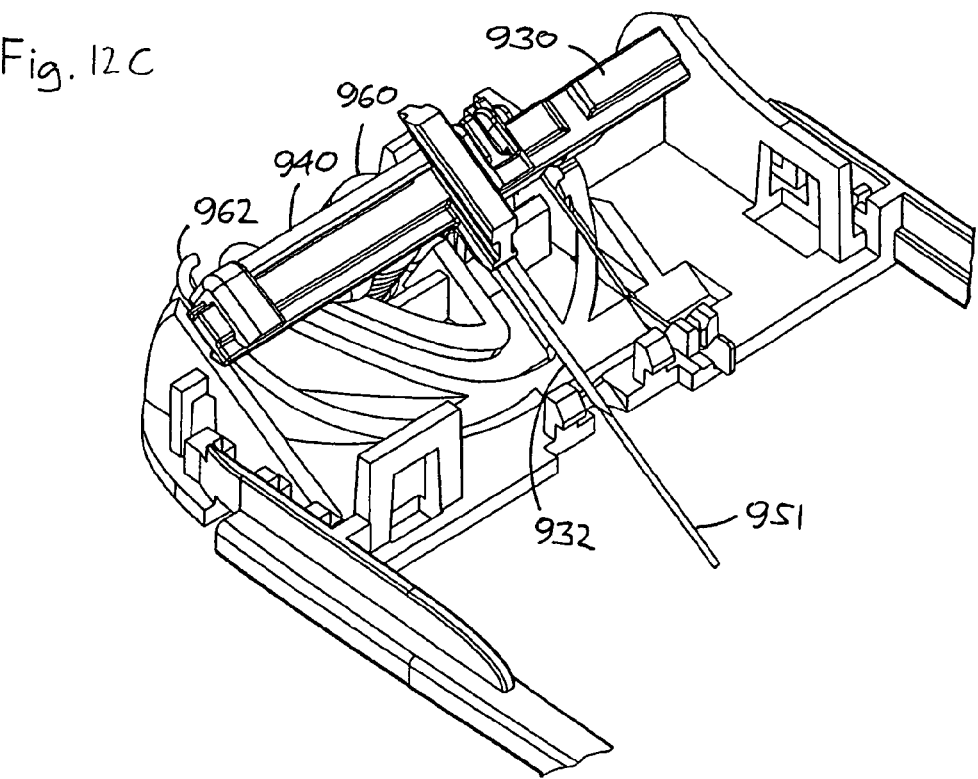

When a pump unit (not shown) is attached to the cannula unit the pump unit engages and pushes the outer end portion 976 of the release member 975, thereby releasing the spring actuator arm 961. The actuator then starts to turn clockwise (as seen in the figure) and engages a rear surface of the needle member pushing it forward to its extended position as seen in FIG. 12B. During this movement the needle holder is guided linearly by engagement with the guide member 921 arranged on an interior surface of the chassis part, whereas the cannula correspondingly is guided linearly to its first extended position by engagement with the first guide groove 913. Thus, during this forward movement, the cannula holder does not move relative to the needle holder.

In this position the needle holder cannot be moved further forward, and as the spring actuator arm continues to turn clockwise it engages the guide member arranged on the lower surface of the cannula holder (not shown, see FIG. 24) thereby starting to move the cannula holder to the left, sliding on the needle holder. At this position the guide member has reached the lower end of the first guide groove (see FIG. 11) and is now moved into the second inclined guide groove where it is moved upwards along the guide groove, thereby being moved further to the left. As the cannula holder is attached to the needle holder, the needle holder is also moved upwards, however, it is guided linearly backwards due to the engagement with the guide member 921. When the cannula holder has reached the upper end of the second guide groove, it has reached its second extended position just as the needle holder has reached its second retracted position (the first and second retracted positions may be the same), just as the cannula holder has reached its second extended position.

As described above, the cannula has a distal portion initially arranged within the needle, an intermediate portion arranged in the channel formed between the cannula and needle holder, and a proximal portion serving as a flexible connection between the moving inserter and the fluid inlet port. As the cannula is attached to the cannula holder corresponding to the proximal end of the intermediate portion, movement to the left of the cannula holder will push the cannula through the channel, around the bend connecting the channel and the needle, and down into the needle. Thus as the cannula holder is moved from its first to its second extended position, the cannula is pushed out through the needle, whereas in the meantime the needle holder with the needle is retracted (see FIG. 12C). In case the cannula and needle are extended respectively retracted at the same speed (this corresponding to the second guide groove being straight and arranged at an angle of 45 degrees relative to the first guide groove) then the distal portion of the extended cannula will not move relative to the housing, whereas the needle will be retracted.

Figure 12D:
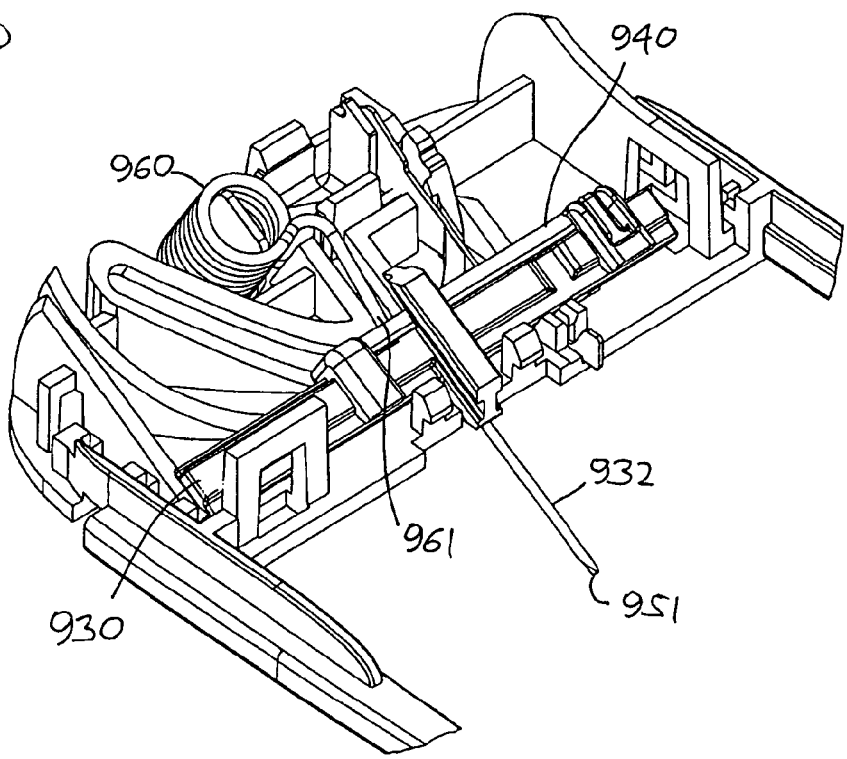

In order to allow the guide member of the cannula holder to properly enter the second guide groove, it may be desirable to connect the two guide grooves with a short groove portion, this providing that the cannula will be extended a little before the needle starts to retract, this as shown in FIG. 12D. Correspondingly, by modifying the configuration of the second guide groove it is possible to retract the cannula a little from its most extended position. The latter may be desirable in order to free a distal cannula opening from any tissue plug formed during insertion.

FIG. 13 shows in an exploded view a pump unit 300 of the same type as in FIG. 9. The pump unit comprises an upper housing portion 310 and a lower housing portion 320 which in an assembled state provides a water-protected enclosure for the additional components of the reservoir unit: A pump assembly 330, an actuator 340, a reservoir 350, and electronic control means 360. In an initial state as supplied to the user, a protective cap assembly 370 is attached to the unit.

The lower housing portion is made from a transparent material allowing a reservoir (see below) to be inspected by a user from the outside, and comprises an opening 321 in which a water repelling vent 322 is arranged. A sheet member 325 with a window opening 326 is attached to the lower surface of the lower housing portion, this masking the transparent portion except for a window over the reservoir. The sheet member may be used to display user information, e.g. type and amount of drug.

The pump assembly 330 is in the form of a membrane pump comprising a piston-actuated pump membrane with flow-controlled inlet- and outlet-valves. The pump has a general layered construction comprising a number of body members between which are interposed flexible membrane layers, whereby a pump chamber, inlet and outlet valves, and one or more safety valves can be formed, the layers being hold together with clamps 338. The pump further comprises a fluid connector 335 in the form of hollow connection needle slidably positioned within the pump (for illustrative purposes shown outside of the pump), this allowing the pump to be connected with reservoir when the protective cap assembly 370 is activated. For a more detailed description of such a membrane pump reference is made to applicants co-pending application WO 2006/089958, which is hereby incorporated by reference.

The pump actuator is in the form of a coil actuator to which the pump assembly is attached by a clamp. For a more detailed description of such a coil actuator reference is made to applicants co-pending application WO 2005/094919, which is hereby incorporated by reference.

The drug reservoir is in the form of a flexible, pre-filled collapsible pouch 350 comprising a needle-penetratable septum 351 allowing the fluid connector to be pushed into the reservoir without leakage, thereby providing a fluid communication with the pump. A clip holder 352 is attached to the reservoir, this allowing the reservoir to be attached to the housing without influencing the reservoir per se. Under the reservoir (as seen from the lower surface of the unit) is arranged a sheet (not shown) comprising a contrast-enhancing pattern, e.g. a black line on a white background, allowing for easier visual identification of impurities in the drug, e.g. fibrillation in insulin.

The electronic control means 360 comprises a PCB or flex-print 362 with a processor 361 for controlling the pump assembly, a battery 366, an acoustic transducer 365 providing an alarm and communication interface with the user, as well as a contact mounted on the actuator allowing the control means to be activated by the user when taken into use for the first time (via the actuator 216). The control means may comprise a receiver and/or a transmitter allowing the reservoir to communicate wirelessly with a remote controller.

The protective cap assembly 370 comprises an attachment member 371 initially locked to the reservoir unit and an activation "push button" member 372 slidingly attached to the attachment member. When the reservoir unit is removed from its primary packaging (not shown) the user depresses the activation member towards the reservoir unit. This actuation results in three actions taking place: A first protrusion on the activation member will actuate a contact on the reservoir unit, this activating the electronics, and a second protrusion will engage the pump assembly and push the fluid connector 335 out from the pump assembly and into the reservoir, thereby establishing a fluid communication between the reservoir and the pump. Thirdly, depression of the activation member will "unlock" the attachment member and allow it, and thereby the activation member, to be removed from the reservoir unit. Thereafter the reservoir unit can be connected to the patch unit.

With reference to FIGS. 14.1-14.5 and 14.7-14.9 the application of a skin-mountable patch device utilizing aspects of the present invention will be described. The description is partly drafted as instructions for a user manual. (1) Pull of the protective paper on the back of the applicator (i.e. the packaging). Make sure to leave the applicator on the patch, as you will need it to attach the patch correctly (see FIG. 14.1). (2) Remove the two pieces of packing paper on the patch—one at a time (the packing paper corresponding to the peel liner 70 in FIG. 2) (see FIG. 14.2). (3) Stand up and attach the patch on the lower abdomen in a rolling movement in the direction of the application arrow. Once attached, press it against the skin (see FIG. 14.3). (4) Slide the applicator off the patch in the direction of the arrow (by this movement the protrusions 101 will slide in the groove 220; when they reach the second end 222 of the groove, the protrusions will be lifted out of the groove and the applicator will become detached from the patch unit. Alternatively, the attachment means can be unlocked by slightly rotating or twisting the applicator). The applicator may be disposed of (see FIG. 14.4). (5) Carefully smooth the patch to the skin by running your fingers gently across the border and in between the sliders (see FIG. 14.5). (6) Remove the pump unit from its packaging. (7) Press down the protective cap to prepare the pump unit for use (see FIG. 14.6). (8) Press and hold the release buttons on the pump. Remove the protective cap (see FIG. 14.8). (9) Slide the pump unit onto the patch. When you feel a click and the pump beeps, the pump is connected correctly. The soft cannula automatically enters the skin (see FIG. 14.9).

As described above with reference to FIG. 1 the flexible sheet 30, 80 may be of any suitable design. In the following a number of examples will be given.

Example 1

2-Zone Hydrocolloid Adhesive on Flexible Permeable Polyurethane Film (Bioflex 25 μ).

Example 2

Adhesive Based on Polypropylene Glycol on Flexible Permeable Polyurethane Film (Bioflex 25 μ).

Example 3

Fixomull Stretch from Bsn Medical-Acrylic Adhesive on Structured Polyester Non-Woven.

Example 4

Two Lyered Construction (See FIG. 2C) of the Materials: 3M/9832, Acrylic Adhesive On Thin Flexible Permeable Polyurethane Film, And 3M/9904, Acrylic Adhesive On Permeable Flexible Polyurethane Non-Woven.

In case of peeling from the edge, it may be possible to prolong the operative life of the skin-mounted device by using a "repair kit" in the form of an adhesive ring for secondary fixation, for example Opsite-Flexifix from Smith & Nephew, an acrylic adhesive on a thin flexible permeable polyurethane film with beneficial supporting backing.

Figure 15:
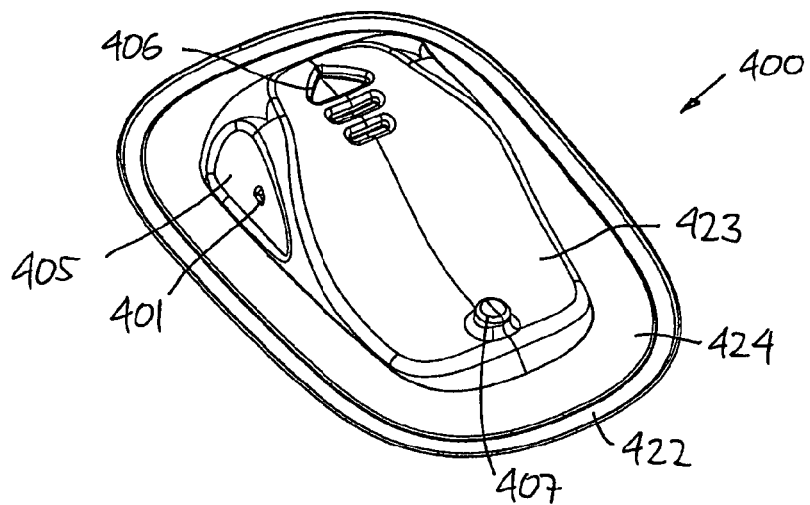
FIGS. 15-17 show a further embodiment of a packaging.
Figure 16:
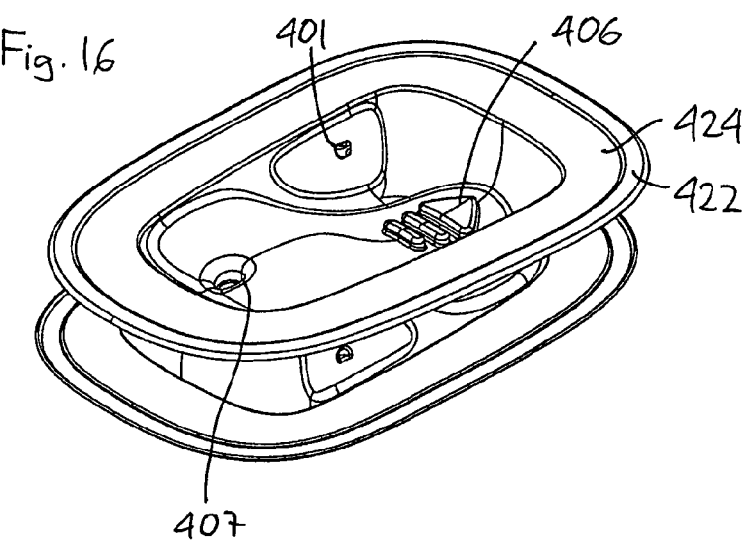
Figure 17:
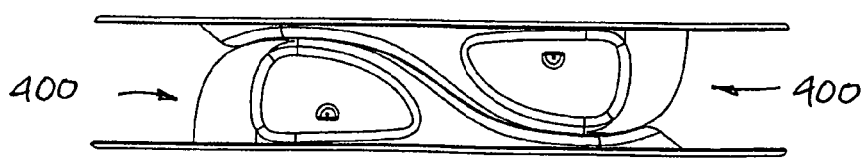

With reference to FIGS. 15-17 a further embodiment of a packaging 400 will be described, the packaging having the same general configuration as the packaging described with reference to FIG. 1. More specifically, the packaging comprises an asymmetrical cavity portion 423 with an indicia 406 at one end of the upper surface, an outer relative flat peripheral portion 424, and a circumferential portion 422. On each side of the packaging a shallow depression 405 is provided on which attachment means in the form of a rounded inwards protrusion 401 is arranged, the two depressions providing first gripping means. In contrast to the above described embodiment, this packaging has an alternative upper surface configuration in which the generally inclined surface is configured so as to allow two assemblies to be arranged on top of each other yin-yang wise as shown in FIG. 17. This configuration allows two packagings to be arranged upon each other in a compact and thus cost-effective way. To further assure that the packagings are "locked" into engagement with each other during e.g. handling and transport, the upper surface is provided with a protrusion 407 at one end adapted to engage the indicia of an opposed packaging.

With reference to FIGS. 18 and 19 a further embodiment of a packaging and a skin-mountable device will be described, the flexible blister packaging 500 having the same general configuration as the packaging described with reference to FIG. 15. More specifically, the packaging comprises an asymmetrical cavity portion 523 with an arrow indicia 506 at one end of the upper surface and a protrusion 507 at the other end, an outer relative flat peripheral portion 524, and a circumferential portion 522. On each side of the packaging a shallow depression 505 is provided on which attachment means in the form of an inwards protrusion 501 is arranged, the two depressions providing first gripping means. In contrast to the above described embodiment, this packaging has a locking means in the form of a ridge 531 arranged below the indicia 506 and adapted to engage a corresponding structure on the skin-mountable device 600, see below. In contrast to the thermo-formed packaging of FIG. 15, the packaging 500 is injection moulded for which reason the protrusion 501 cannot be seen as a depression on the outer surface.

The skin-mountable device 600 is of the same general configuration as the device 200 of FIG. 7 (the flexible sheet member not being shown), i.e. comprising a body portion with a housing portion 612 from which two leg members 613 extend. The housing portion comprises a protrusion 619 in front of which a groove 629 is formed. However, in contrast to the groove structure 220 adapted to cooperate with the packaging protrusions 101 of FIG. 6, this embodiment comprises a pair of opposed ridge structures 620 adapted to cooperate with the packaging protrusions 501 of FIG. 18. In the shown embodiment a "channel" 621 is formed in front of each ridge structure. In an initial position as supplied to the user (not shown), the protrusions 501 are arranged below and in contact with the ridge structures 620, this preventing the two units to be moved away from each other in a direction perpendicularly to the general plane. To prevent that the protrusions inadvertently disengage form the ridge structures during e.g. handling or transport, the ridge 531 is in the initial position positioned in the groove 629, this providing a locking means securing the two units against inadvertent movement in the above-described first direction.

In a situation of use, after the skin-mountable device has been arranged on a skin surface, the user will start to slide the packaging in the direction of the indicia 506 whereby the ridge 531 is lifted out of the groove 629 and the blister protrusions 501 is moved away from engagement with the ridge structures 620. As the blister packaging is slightly deformed as the ridge 531 is moved out of engagement with the groove 629, the deformation can be used to exert an upward pulling force on the blister protrusions 501 whereby they will disengage the ridge structures 620 with a "snap" sound, this indicating to the user that the two units have disengaged from each other and that the packaging can now be moved away from the skin-mounted device, the protrusions thereby sliding through the channel areas 621. Indeed, in an alternative configuration the area in front of the ridge structures could be planar or in the form of a groove as long as the blister is allowed to be moved away from the skin surface.

As appears, whereas the blister packaging of the embodiment of FIGS. 4-6 was intended to be removed by a sliding action of the blister packaging in parallel with the skin surface, the blister packaging of the embodiment of FIGS. 18 and 19 is operated by first sliding the blister a relatively short distance in parallel with the skin surface to thereby disengage the two parts after which it can be lifted away from the skin-mounted device in a direction away from the skin surface.

In the above description of the preferred embodiments, the different structures and means providing the described functionality for the different components have been described to a degree to which the concept of the present invention will be apparent to the skilled reader. The detailed construction and specification for the different components are considered the object of a normal design procedure performed by the skilled person along the lines set out in the present specification.

The invention claimed is:

1. An assembly for mounting a skin-mountable device, the assembly comprising:
    a) a skin-mountable device having an adhesive mounting surface defining a first plane for mounting the skin-mountable device to a selected area of skin;
    b) a blister package configured to releasably receive and surround the skin-mountable device within an interior cavity defined by a plurality of package walls, wherein the package has an aperture through which the skin-mountable device moves when it is detached from the package; and
    c) a connecting structure comprising a linear guide that allows the entire package when in a connected state with the skin-mountable device to move a predetermined distance relative to the skin-mountable device in a first direction parallel to the first plane when a force is applied to the package in the first direction before continued movement of the entire package in the first direction causes the package to release the skin-mountable device.

2. The assembly as in claim 1, wherein the linear guide comprises a pair of opposed protrusions on either the package or the skin-mountable device, and a pair of opposed cooperating grooves arranged on the other of the package and the skin-mountable device.

3. The assembly as in claim 1, wherein further application of a force to the package in the first direction results in disengagement of the connecting structure, allowing the package to be moved away from the first plane.

4. The assembly as in claim 3, wherein further application of a force to the package in the first direction results in engagement between an inner inclined surface of the package and an upper surface of the skin-mountable device.

5. The assembly as in claim 1, wherein the package grips the connecting structure, whereby application of a force moves the connecting structure into engagement with each other.

6. The assembly as in claim 1, wherein the package comprises a release associated with the connecting structure, whereby application of a force to the release forces the connecting structure from engagement with each other.

7. The assembly as in claim 1, wherein the connecting structure comprises a pair of opposed protrusions on either the package or the skin-mountable device, and a pair of opposed cooperating structures arranged on the other of the package and the skin-mountable device.

8. The assembly as in claim 1, comprising a releasable lock for securing an initial position in which the package and the skin-mountable device is attached to each other.

9. The assembly as in claim 8, wherein the lock is released when the package is moved relative to the skin-mountable device in the first direction.

10. The assembly as in claim 1, wherein the package comprises a portion surrounding the aperture, and a seal member releasably attached to the surrounding portion, thereby providing a sealed space for the skin-mountable device.

11. The assembly as in claim 1, wherein the mounting surface comprises an adhesive for adhering the skin-mountable device to the skin of the subject, the adhesive being covered by a releasably attached protective structure, and wherein the package comprises a portion surrounding the aperture and a seal member releasably attached to the surrounding portion, thereby providing a sealed space for the skin-mountable device.

12. The assembly as in claim 10, wherein removal of the seal member results in a protective structure being removed from the adhesive.

13. The assembly as in claim 10, wherein the seal member has an inner surface releasably attached to the adhesive, the seal member thereby providing a protective structure.

14. The assembly as in claim 13, wherein the seal is penetratable by a sterilizing gas, and wherein the inner surface is partially coated with a material allowing the seal member to be peeled from the adhesive, and allows the sterilizing gas to penetrate the seal member.

15. The assembly as in claim 1, the skin-mountable device further comprising a transcutaneous device comprising a distal end adapted to be inserted through the skin of a subject, the distal end being moveable between an initial position in which the distal end is retracted relative to the mounting surface, and an extended position in which the distal end projects relative to the mounting surface.

16. The assembly as in claim 15, wherein the transcutaneous device is provided in combination with a pointed insertion needle being retractable relative to the transcutaneous device.

17. The assembly as in claim 15, wherein the skin-mountable device comprises an actuator for moving the distal end of the transcutaneous device between the initial and the extended position when the actuator is actuated.

18. The assembly as in claim 1, wherein the skin-mountable device is actuatable between an initial state and an actuated state, and wherein the skin-mountable device and the package comprises a cooperating actuator such that the skin-mountable device is actuated when the package is removed from the skin-mountable device.

19. A system comprising two assemblies as in claim 1, wherein an upper portion of the package has an outer generally inclined surface, the generally inclined surface being configured so as to allow two assemblies to be oppositely arranged on top of each other.

20. A system comprising an assembly as in claim 1, in combination with a second device, wherein the second device and the skin-mountable device comprises a connecting structure.

21. The system as in claim 20, wherein the skin-mountable device comprises a transcutaneous device in the form of a transcutaneous sensor device, and the second device comprises a processor adapted to transmit or process data acquired via the sensor device.

22. The system as in claim 20, wherein the skin-mountable device comprises a transcutaneous device in the form of a transcutaneous access device, and the second device comprises a reservoir adapted to contain a fluid drug, an expelling assembly adapted for cooperation with the reservoir to expel fluid drug out of the reservoir and through the skin of the subject via the transcutaneous access device, and a processor for controlling the expelling assembly.

23. The system as in claim 21, wherein the transcutaneous device comprises a distal end adapted to be inserted through the skin of a subject, the distal end being moveable between an initial position in which the distal end is retracted relative to the mounting surface, and an extended position in which the distal end projects relative to the mounting surface.

\* \* \* \* \*